US009101432B2

(12) United States Patent
Limouze et al.

(10) Patent No.: US 9,101,432 B2
(45) Date of Patent: Aug. 11, 2015

(54) SUPRAPATELLAR INSERTION SYSTEM, KIT AND METHOD

(71) Applicant: DePuy Synthes Products, Inc., Raynham, MA (US)

(72) Inventors: Robert Limouze, West Chester, PA (US); Sean Powell, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/729,572

(22) Filed: Dec. 28, 2012

(65) Prior Publication Data

US 2013/0172890 A1 Jul. 4, 2013

Related U.S. Application Data

(60) Provisional application No. 61/581,529, filed on Dec. 29, 2011.

(51) Int. Cl.
A61B 17/56 (2006.01)
A61B 17/90 (2006.01)
(Continued)

(52) U.S. Cl.
CPC ........... A61B 17/921 (2013.01); A61B 17/1717 (2013.01); A61B 17/1725 (2013.01); A61B 17/72 (2013.01); A61B 17/8872 (2013.01)

(58) Field of Classification Search
CPC .. A61B 17/921; A61B 17/72; A61B 17/1717; A61B 17/3468
USPC ....... 606/62–68, 79–80, 86 R, 87–89, 95–99, 606/104; 600/201–212; 604/158, 164.01, 604/533, 165.01, 165.02
See application file for complete search history.

(56) References Cited

U.S. PATENT DOCUMENTS 4,466,429 A * 8/1984 Loscher et al. ............... 606/180
4,865,025 A 9/1989 Buzzi et al.
(Continued)

FOREIGN PATENT DOCUMENTS

| CN | 2922822 | 7/2007 |
|---|---|---|
| DE | 198 60 569 | 8/2000 |
| DE | 102008004922 | 10/2009 |

OTHER PUBLICATIONS

International Patent Application No. PCT/US2012/071987: International Search Report and Written Opinion dated Mar. 14, 2013, 15 pages.

Primary Examiner — Eduardo C Robert
Assistant Examiner — Jacqueline Johanas
(74) Attorney, Agent, or Firm — Baker & Hostetler LLP

(57) ABSTRACT

A system is provided for inserting and securing, through a suprapatellar region of a leg, a nail into a medullary canal of a bone. The system can include a flexible sleeve configured to be partially inserted in the leg. The flexible sleeve can define a leading end and a trailing end spaced apart from the leading end along a first axis. The flexible sleeve can define a first cannulation that extends along the first axis between the leading and trailing ends. The first cannulation can be sized to receive therethrough at least the intramedullary nail. The system can further include a retaining member configured support at least a portion of the flexible sleeve. The retaining member can be configured to position the flexible sleeve through the suprapatellar region of the leg such that the flexible sleeve leading end is aligned with the proximal end of the bone. The intramedullary nail can be insertable through the flexible sleeve and into the medullary canal.

35 Claims, 20 Drawing Sheets

(51) Int. Cl.
*A61B 17/92* (2006.01)
*A61B 17/72* (2006.01)
*A61B 17/17* (2006.01)
*A61B 17/88* (2006.01)

(56) References Cited

U.S. PATENT DOCUMENTS

| | | | |
|---|---|---|---|
| 4,927,424 A * | 5/1990 | McConnell et al. | 606/96 |
| 5,374,271 A | 12/1994 | Hwang | |
| 5,443,469 A | 8/1995 | Smith | |
| 5,624,447 A * | 4/1997 | Myers | 606/96 |
| 5,766,180 A * | 6/1998 | Winquist | 606/104 |
| 5,800,437 A | 9/1998 | Gustilo et al. | |
| 5,814,049 A * | 9/1998 | Pratt et al. | 606/80 |
| 5,904,685 A | 5/1999 | Walawalkar | |
| 5,951,561 A * | 9/1999 | Pepper et al. | 606/80 |
| 6,036,657 A * | 3/2000 | Milliman et al. | 600/564 |
| 6,074,392 A * | 6/2000 | Durham | 606/67 |
| 6,093,192 A | 7/2000 | Abel | |
| 6,117,151 A * | 9/2000 | Urich et al. | 606/169 |
| 6,206,880 B1 | 3/2001 | Karladani | |
| 6,371,959 B1 * | 4/2002 | Trice | 606/97 |
| 6,419,678 B1 * | 7/2002 | Asfora | 606/96 |
| 6,547,791 B1 | 4/2003 | Buhren et al. | |
| 6,613,065 B2 * | 9/2003 | Lajtai | 606/190 |
| 6,656,189 B1 | 12/2003 | Wilson et al. | |
| 6,926,720 B2 | 8/2005 | Castaneda | |
| 7,033,363 B2 | 4/2006 | Powell et al. | |
| 7,033,365 B2 | 4/2006 | Powell et al. | |
| 7,175,631 B2 * | 2/2007 | Wilson et al. | 606/97 |
| 7,175,633 B2 * | 2/2007 | Roth et al. | 606/99 |
| 7,179,259 B1 | 2/2007 | Gibbs | |
| RE39,995 E * | 1/2008 | Pepper et al. | 606/80 |
| 7,422,594 B2 * | 9/2008 | Zander | 606/80 |
| 7,476,225 B2 | 1/2009 | Cole | |
| 7,887,548 B2 * | 2/2011 | Usher et al. | 606/104 |
| 8,287,538 B2 * | 10/2012 | Brenzel et al. | 606/62 |
| 8,287,539 B2 * | 10/2012 | Nelson et al. | 606/62 |
| 8,328,805 B2 * | 12/2012 | Cole | 606/62 |
| 2003/0004513 A1 * | 1/2003 | Guzman et al. | 606/62 |
| 2003/0135211 A1 | 7/2003 | Cho | |
| 2004/0167533 A1 * | 8/2004 | Wilson et al. | 606/97 |
| 2004/0243138 A1 * | 12/2004 | Cole | 606/99 |
| 2005/0261555 A1 * | 11/2005 | Guzman et al. | 600/204 |
| 2008/0264109 A1 * | 10/2008 | Ritchey et al. | 66/88 |
| 2008/0269744 A1 | 10/2008 | Kay et al. | |
| 2008/0269751 A1 | 10/2008 | Matityahu | |
| 2008/0287950 A1 | 11/2008 | Frigg et al. | |
| 2008/0294172 A1 * | 11/2008 | Baumgart | 606/99 |
| 2008/0306485 A1 | 12/2008 | Coon et al. | |
| 2009/0043309 A1 * | 2/2009 | Rasmussen | 606/88 |
| 2009/0043310 A1 * | 2/2009 | Rasmussen | 606/88 |
| 2009/0099566 A1 | 4/2009 | Maness et al. | |
| 2009/0112268 A1 | 4/2009 | Cole | |
| 2009/0149861 A1 * | 6/2009 | Brodsky et al. | 606/96 |
| 2009/0248024 A1 | 10/2009 | Edwards et al. | |
| 2010/0211073 A1 | 8/2010 | Merrell | |
| 2010/0286696 A1 * | 11/2010 | Christie et al. | 606/80 |
| 2011/0077657 A1 | 3/2011 | Karasik | |
| 2011/0125200 A1 | 5/2011 | Hanson et al. | |
| 2011/0245885 A1 | 10/2011 | Powell | |
| 2013/0190570 A1 * | 7/2013 | Hirsch et al. | 600/204 |
| 2013/0310886 A1 | 11/2013 | Vanosten | |

\* cited by examiner

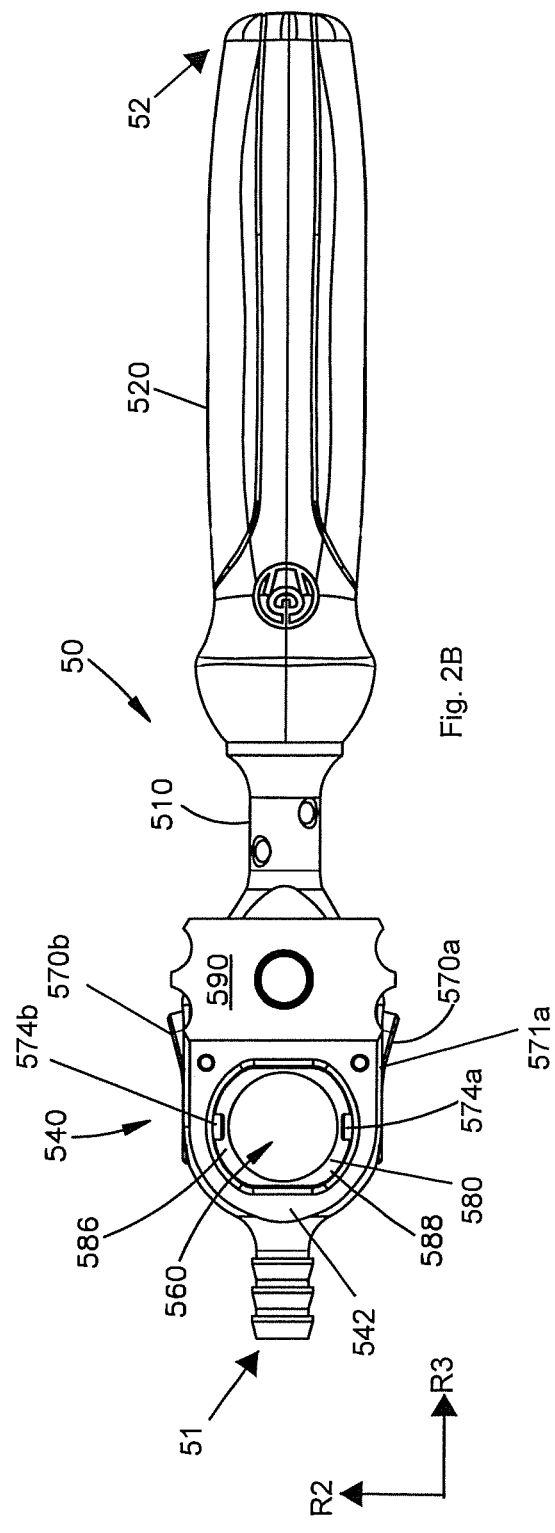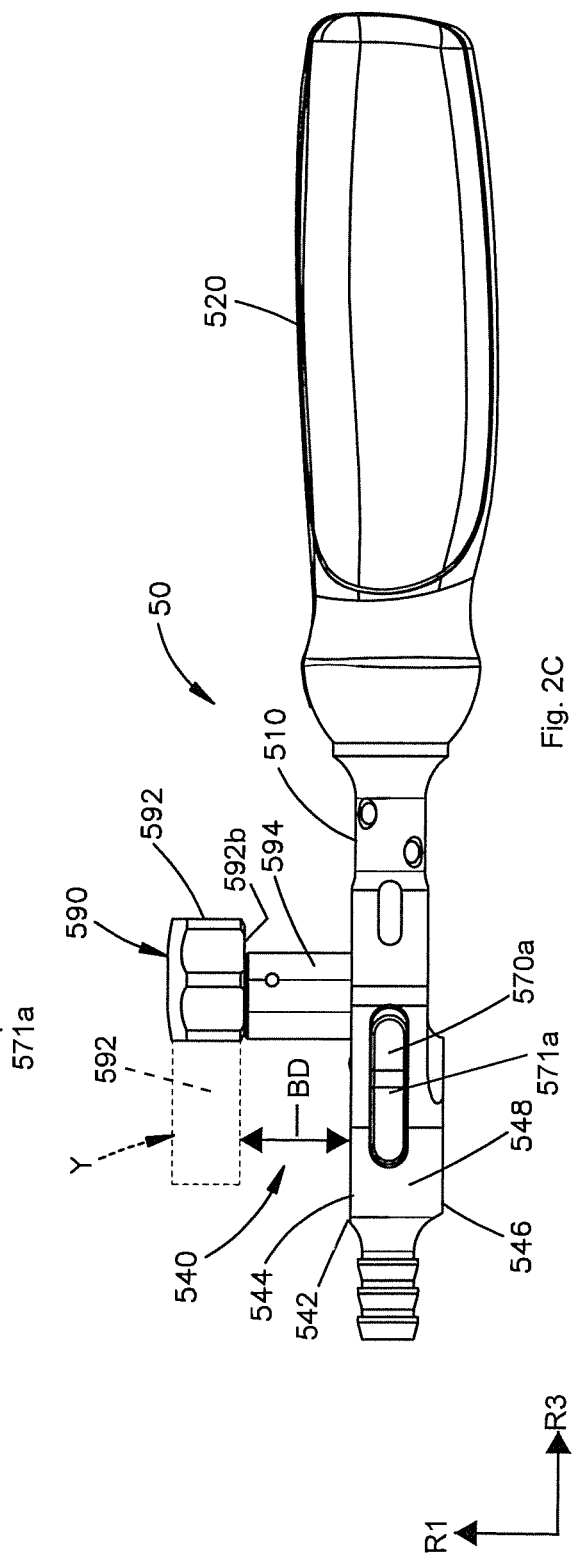

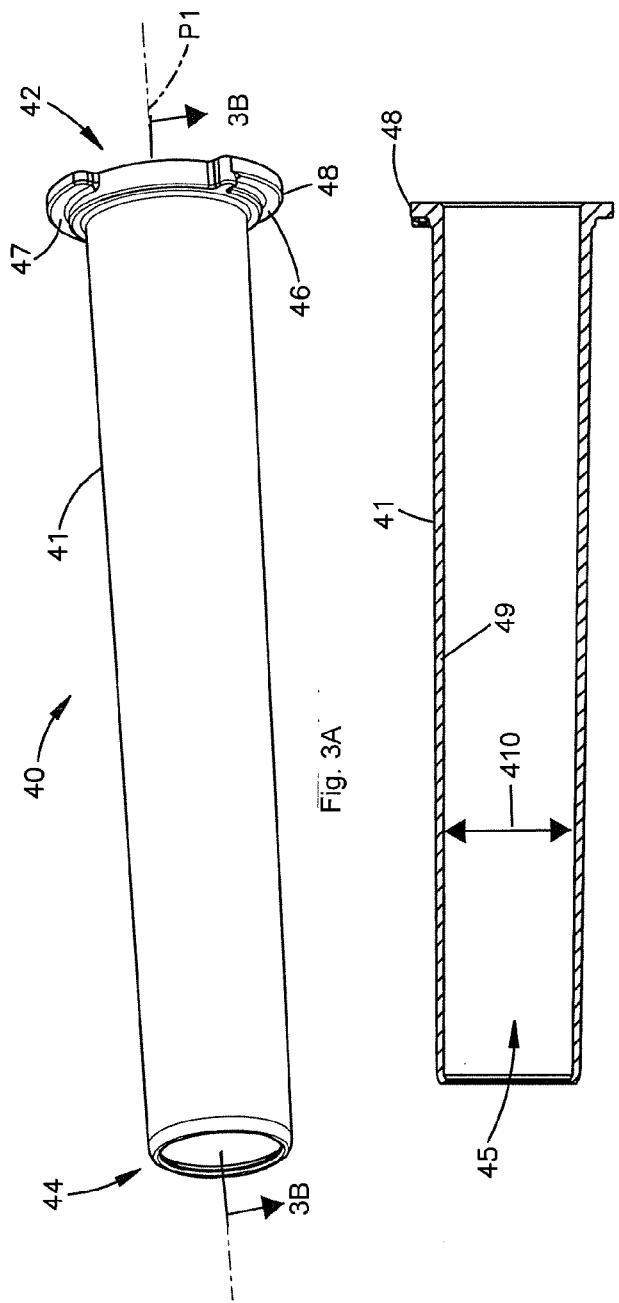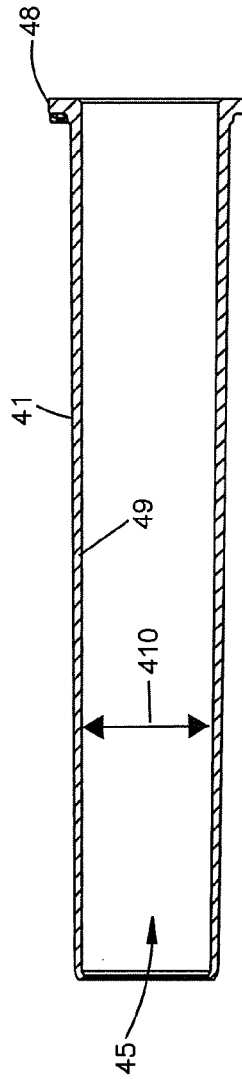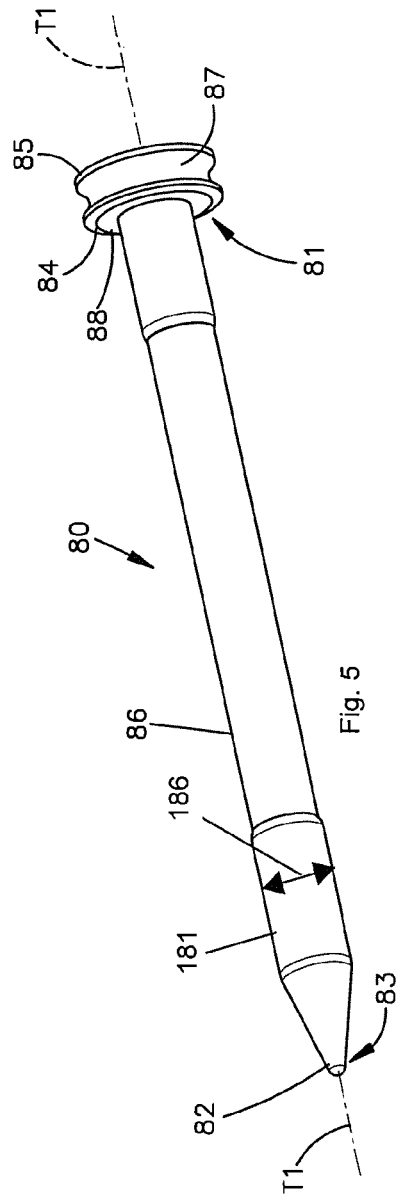

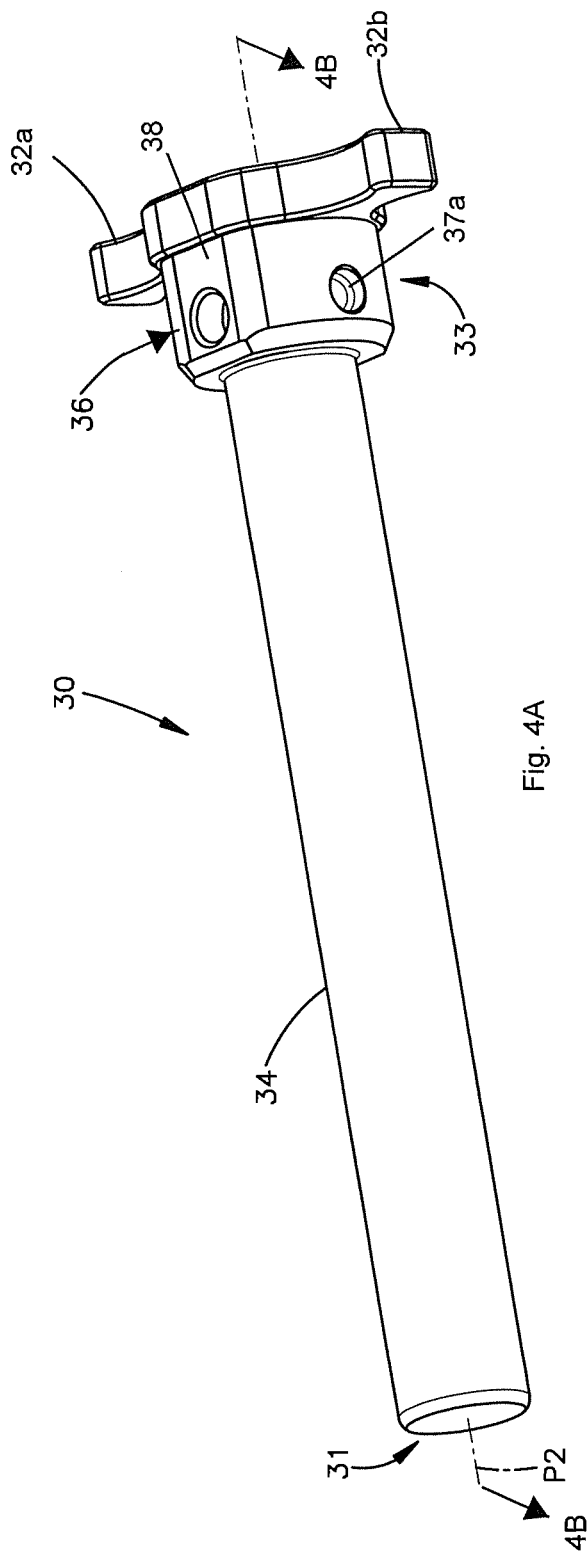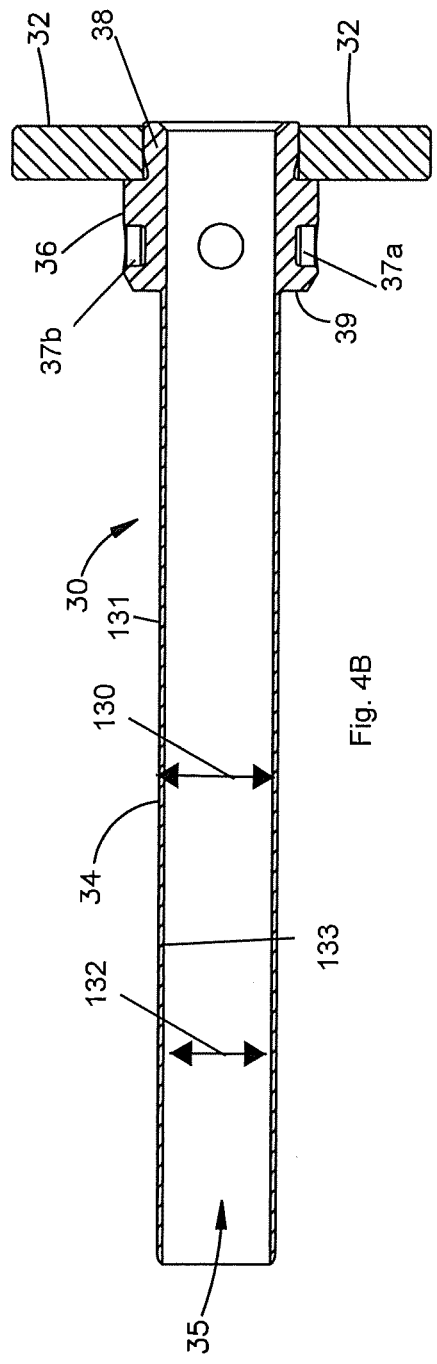
Fig. 4A
Fig. 4B

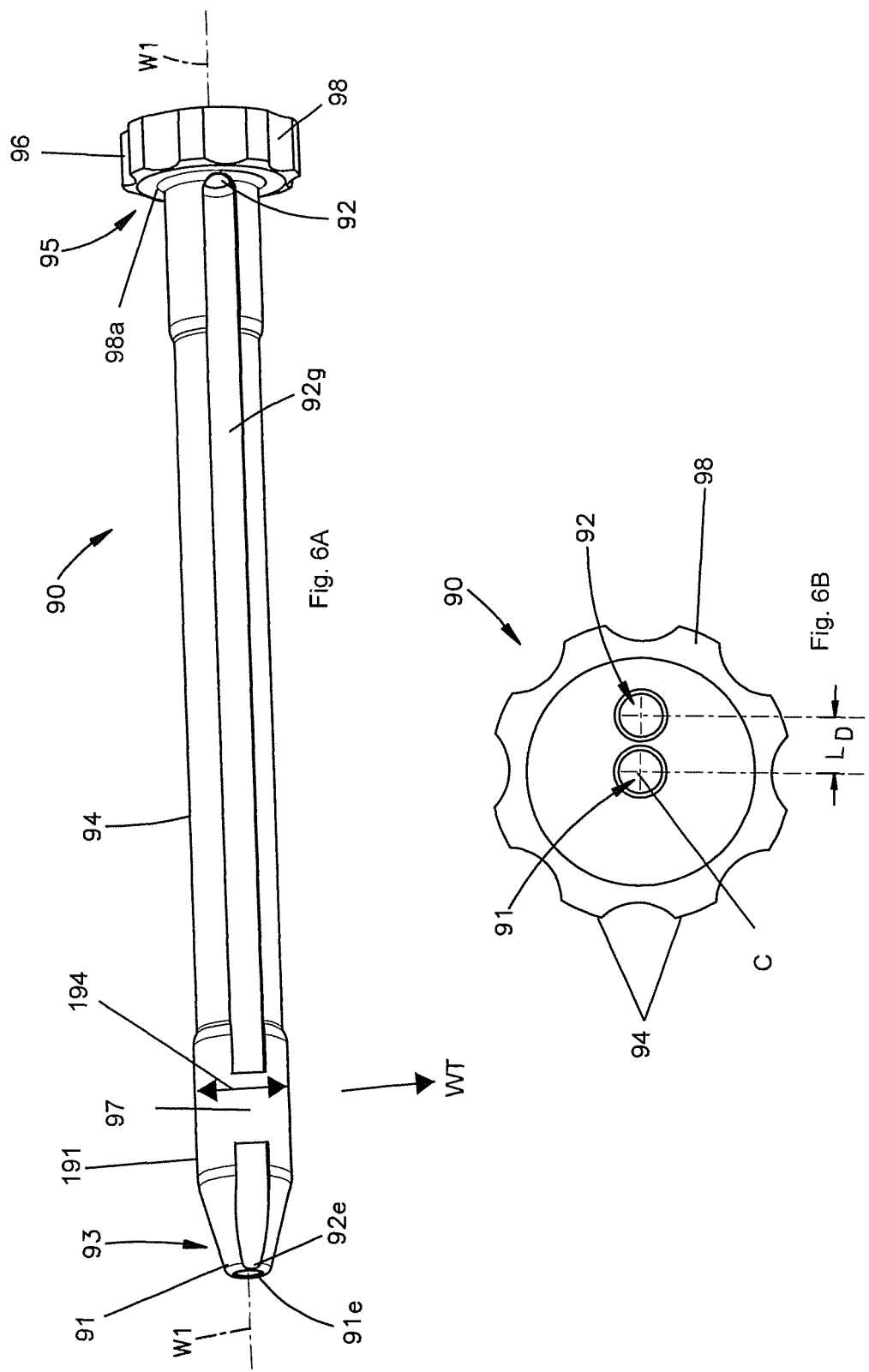

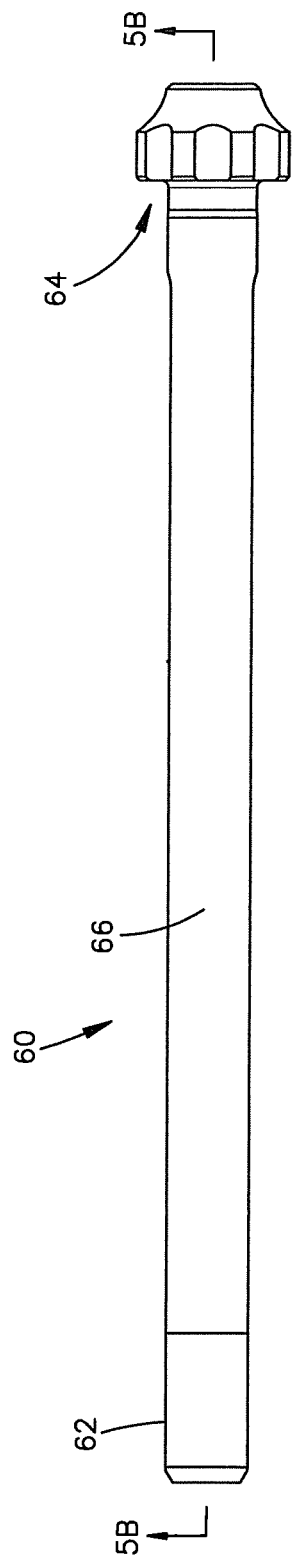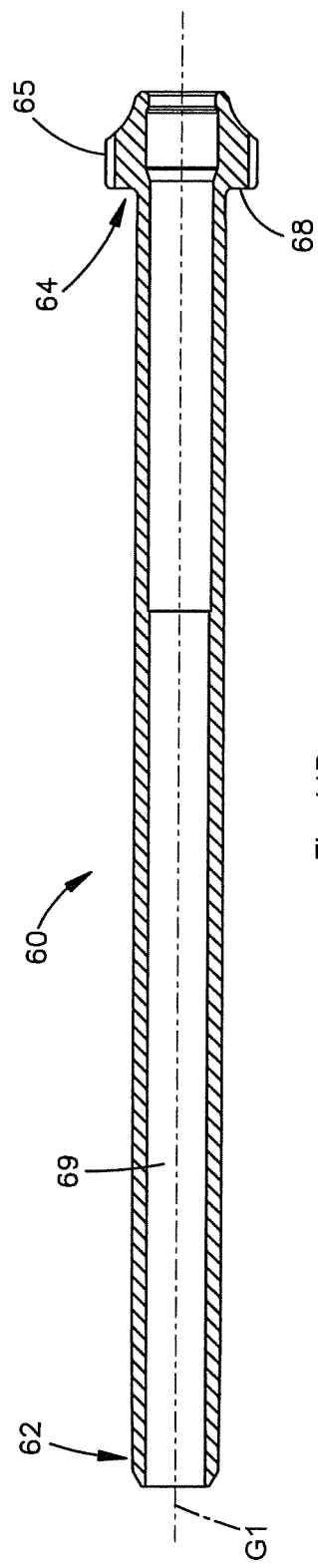
Fig. 11A
Fig. 11B

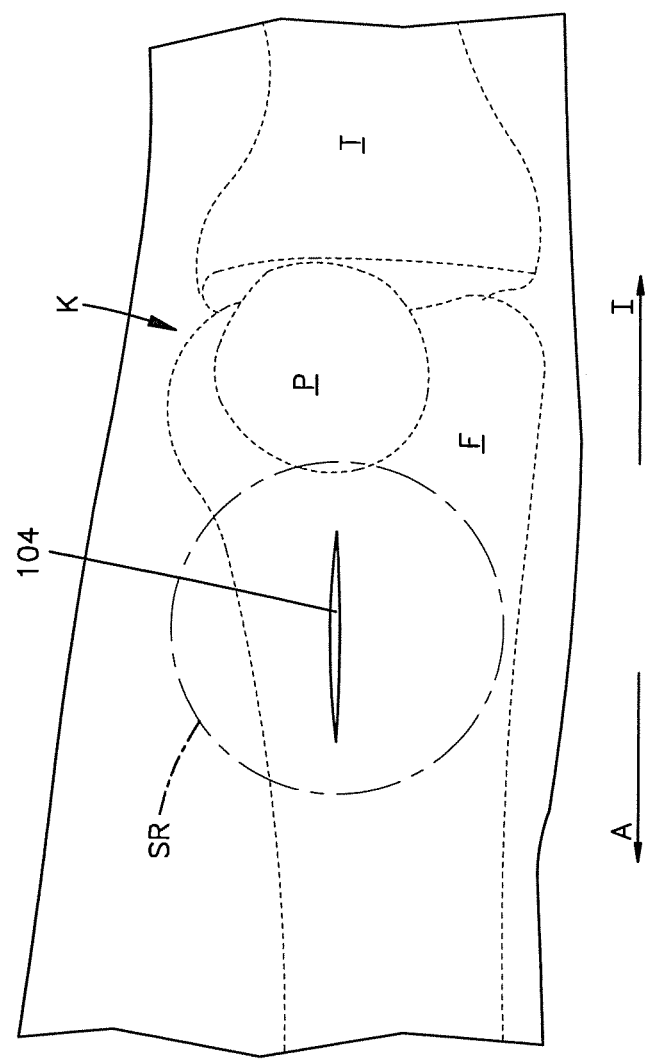

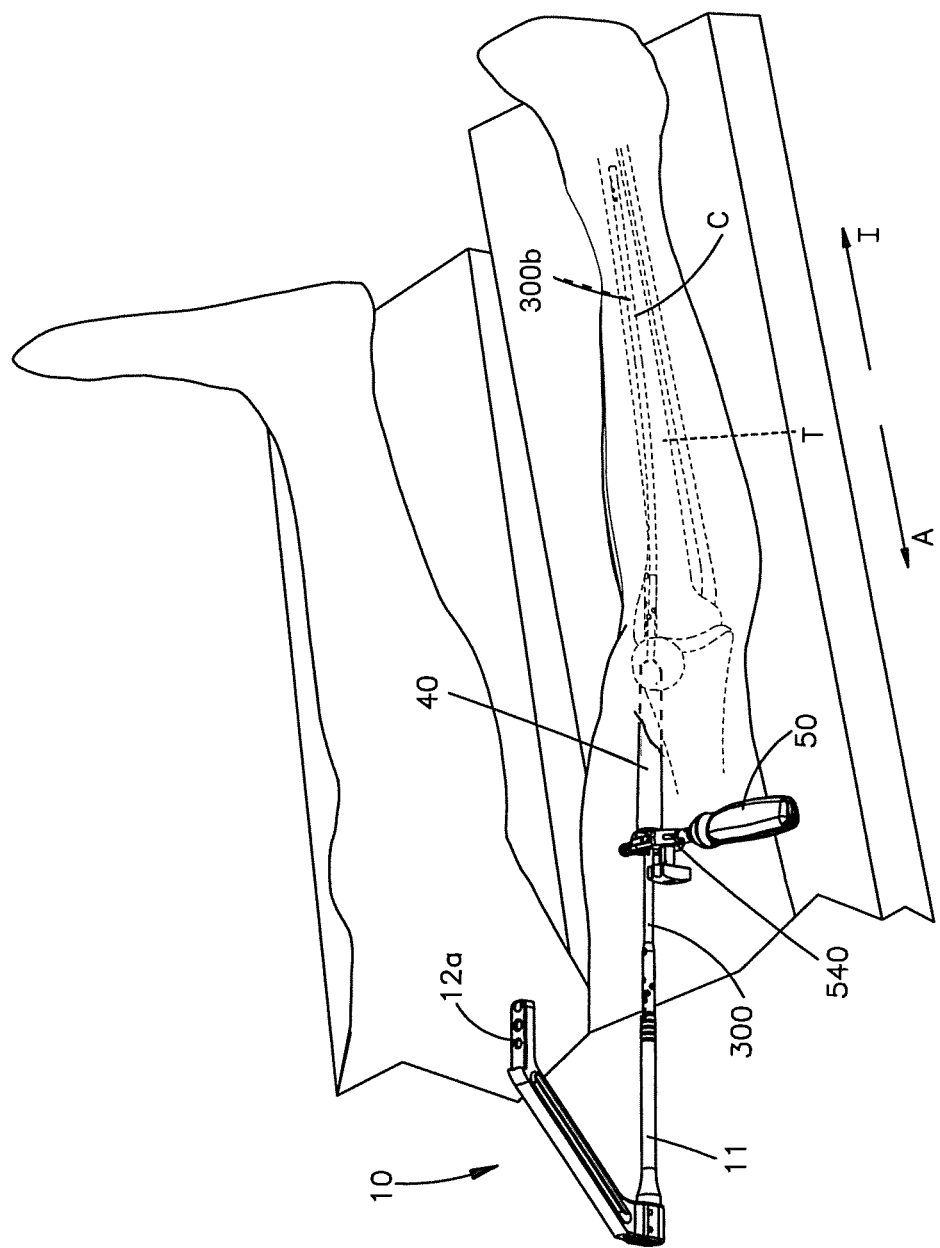

SUPRAPATELLAR INSERTION SYSTEM, KIT AND METHOD

CROSS-REFERENCE TO RELATED APPLICATIONS

This application claims priority to U.S. Application Ser. No. 61/581,529, filed Dec. 29, 2011, entitled "Suprapatellar Kit and Method," the entirety of which is incorporated herein by reference for all purposes.

TECHNICAL FIELD

The present disclosure relates to a system, kit and method for the insertion and fixation of a nail into a medullary canal of a bone.

BACKGROUND

A nail may be inserted into a medullary canal of the bone to secure together bone fragments of a tibia separated by a fracture. The intramedullary nail is inserted into the canal such that nail spans the fracture. Anchors can be inserted through the bone and into the intramedullary nail at opposing sides of the fracture, thereby fixing the intramedullary nail to the bone. The intramedullary nail can remain in the medullary canal at least until the fracture is fused. In one exemplary method, a intramedullary nail is inserted into the medullary canal of the tibia while the patient's knee is bent at a 90 degree angle. When the knee is bent to 90 degrees during nail insertion, the quadriceps muscle pulls the proximal bone fragment askew relative to the distal bone fragment and bone fragment misalignment can occur. Inserting the intramedullary nail while the patient's knee is bent at a 10-20 degree angle can reduce the risk of bone fragment misalignment because the quadriceps muscle does not pull the proximal bone fragment of the bone to such an extent compared to when the knee is bent at a 90 degree angle or more.

There is a need for an improved system, kit and method for inserting a nail into a bone, and the subsequent fixation of the intramedullary nail to the bone.

SUMMARY

In accordance with an embodiment of the present disclosure, a system is provided for inserting and securing, through a suprapatellar region of a leg, a nail into a medullary canal of a bone. The system can include a flexible sleeve configured to be partially inserted in the leg. The flexible sleeve can define a leading end and a trailing end spaced apart from the leading end along a first axis. The flexible sleeve can define a first cannulation that extends along the first axis between the leading and trailing ends. The first cannulation can be sized to receive therethrough at least the intramedullary nail. The system can further include a retaining member configured support at least a portion of the flexible sleeve. The retaining member can be configured to position the flexible sleeve through the suprapatellar region of the leg such that the flexible sleeve leading end is aligned with the proximal end of the bone. The intramedullary nail can be insertable through the flexible sleeve and into the medullary canal.

BRIEF DESCRIPTION OF THE DRAWINGS

The foregoing summary, as well as the following detailed description of a preferred embodiment, are better understood when read in conjunction with the appended diagrammatic drawings. For the purpose of illustrating the present disclosure, reference to the drawings is made. The scope of the disclosure is not limited, however, to the specific instrumentalities disclosed in the drawings. In the drawings:

FIG. 2B is a plan view of the retaining device shown in FIG. 2A;

FIG. 2C is a side view the retaining device shown FIG. 2A;

FIGS. 3A and 3B are perspective and sectional views, respectively, of a flexible sleeve used with the system shown in FIG. 1;

FIGS. 4A and 4B are perspective and sectional views, respectively, of a rigid sleeve used with the system shown in FIG. 1;

FIG. 5 is a perspective view of a trocar used with the system shown in FIG. 1;

FIG. 6A is a perspective view of a wire guide used with the system shown in FIG. 1;

FIG. 6B is an end view of the wire guide shown in FIG. 6A;

FIGS. 11A and 11B are side and sectional views, respectively of a guide sleeve used in the system shown in FIG. 1;

FIGS. 12A and 12B illustrate the right leg of a patient prepared for receiving an intramedullary nail into the medullary canal of the bone in accordance with an embodiment of the present disclosure;

FIG. 17 is a perspective view illustrating how the insertion device is used to insert an intramedullary nail through the flexible sleeve and into a medullary canal of a tibia in accordance with an embodiment of the present disclosure.

DETAILED DESCRIPTION

Figure 1:
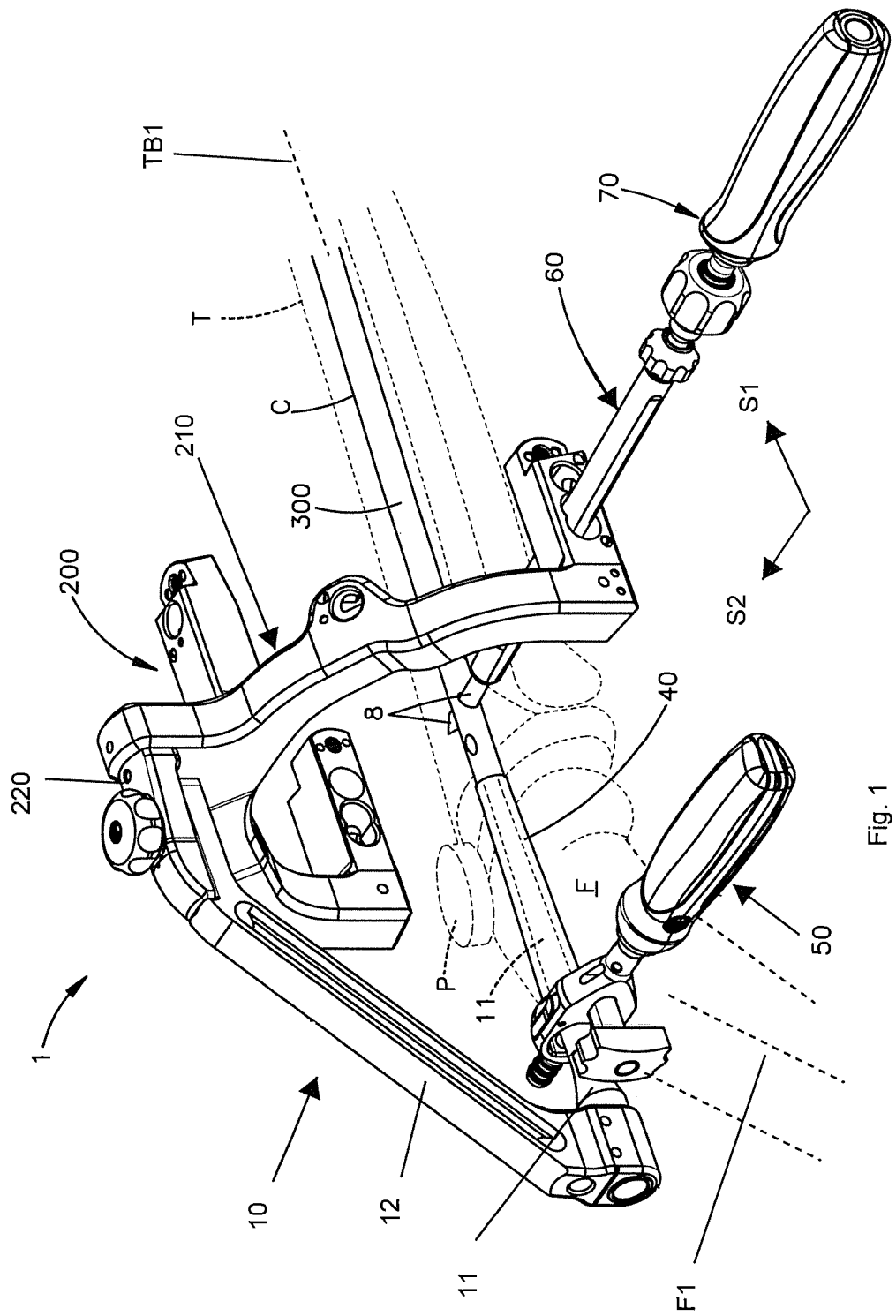
FIG. 1 is a perspective view of a system used to insert an intramedullary nail into a medullary canal of a bone through a suprapatellar region of a leg, in accordance with an embodiment of the present disclosure.
Figure 7A:
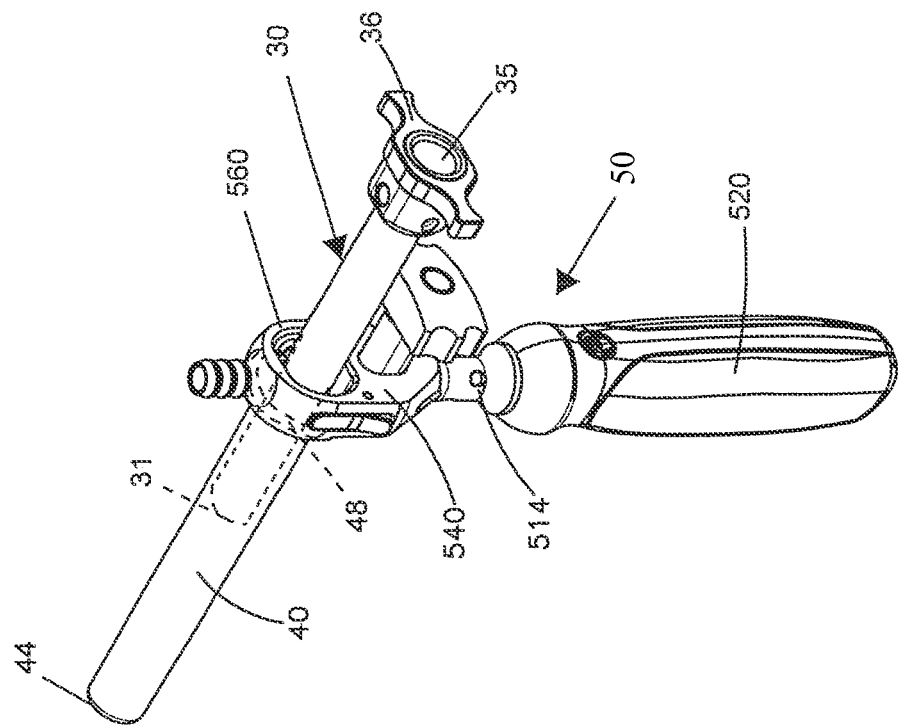
FIGS. 7A and 7B illustrate a retaining device holding a flexible sleeve with the rigid sleeve inserted in the flexible sleeve, in accordance with an embodiment of the present disclosure.
Figure 12A:
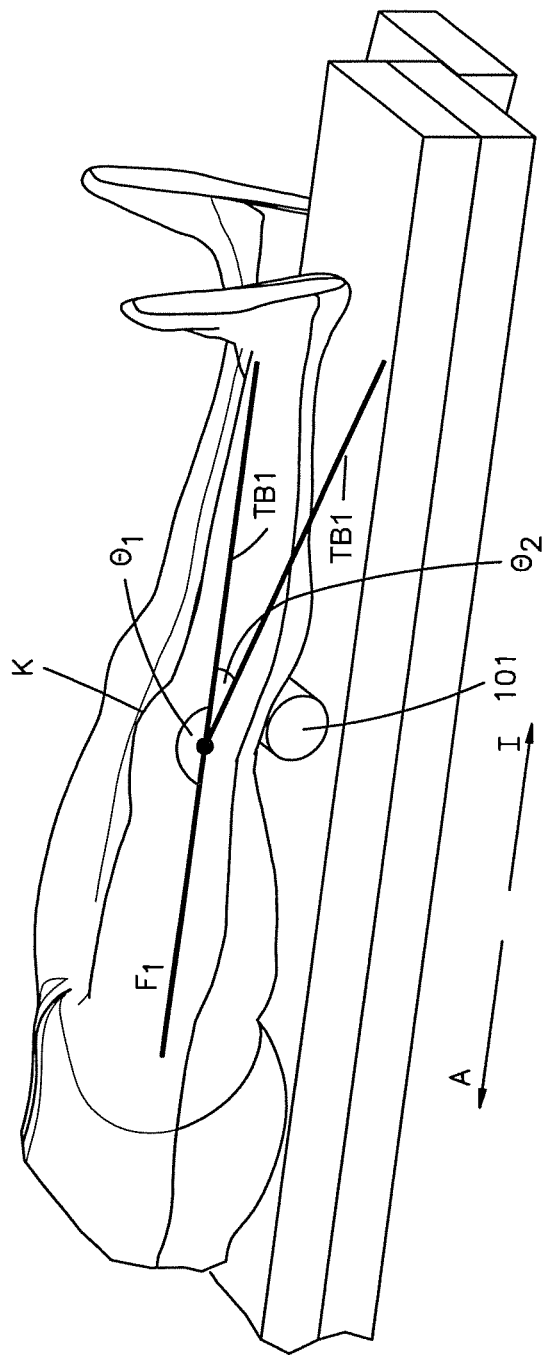
Figure 15:
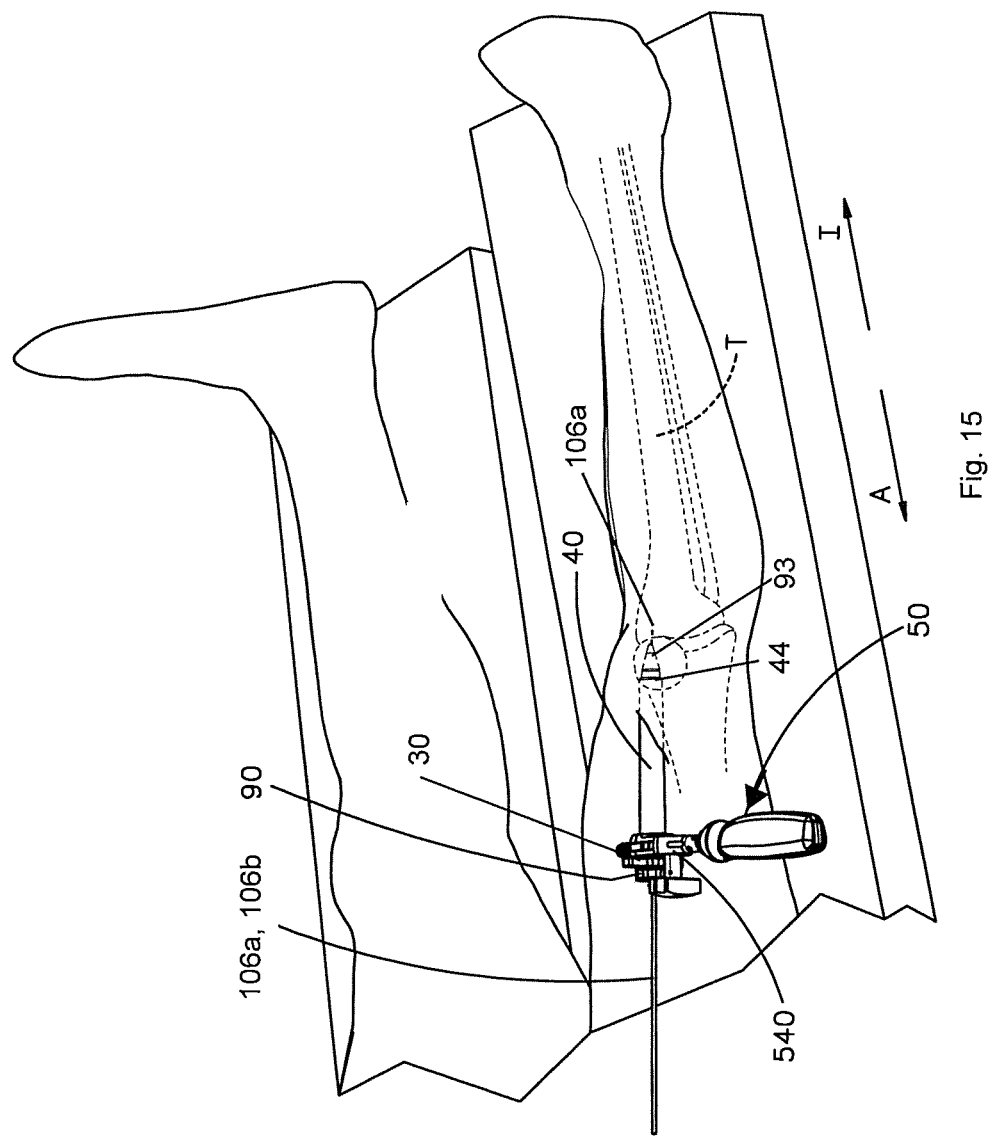
FIG. 15 illustrates the retaining device supporting the flexible sleeve, the rigid sleeve, and a wire guide inserted in the rigid and flexible sleeves, with a wire positioned in the wire guide, in accordance with an embodiment of the present disclosure.
Figure 16:
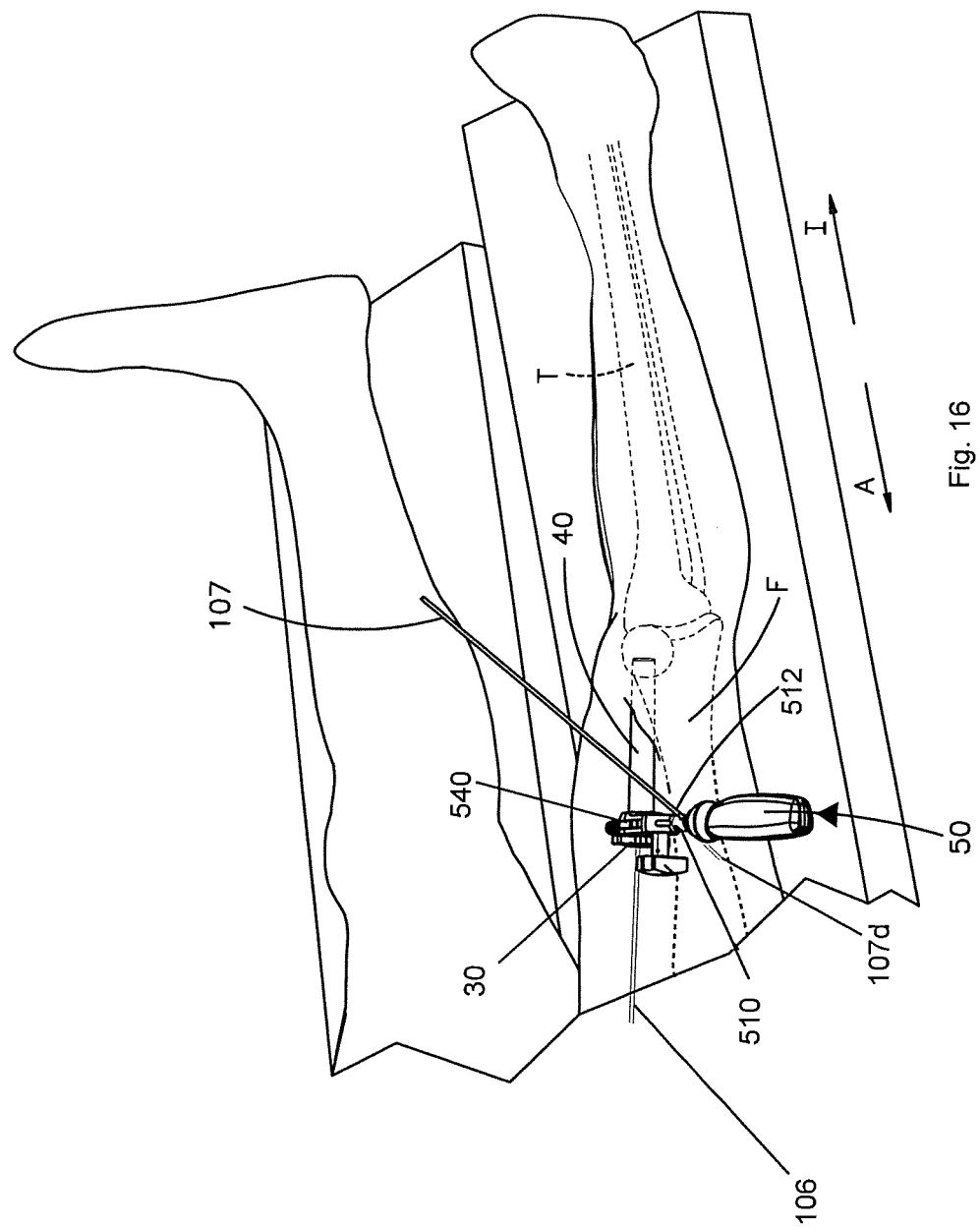
FIG. 16 illustrates the retaining device supporting the flexible sleeve and the rigid sleeve, with an additional wire coupling the retaining device to the femur of a the leg, with the rigid sleeve positioned to receive additional instrumentation therein, in accordance with an embodiment of the present disclosure.

Referring generally to FIGS. 1 and 7A, the system 1 is configured to prepare a medullary canal C of a bone T in a leg, insert an intramedullary nail 300 (sometimes referred to herein as a "nail") into the medullary canal C when the knee is flexed to between 10 and 20 degrees flexion as shown in FIGS. 1 and 12, and subsequently fix the intramedullary nail 300 to the bone T. The bone T can define a proximal end and a distal end spaced apart from the proximal end along an axis TB1. A superior-inferior direction S1 or first direction extends along the axis TB1. The femur F can have a femur axis F1 and the degree of flexion is defined by the angle formed by the femur axis F1 and the bone axis TB1. The system 1 can include a retaining device 50 (FIGS. 2A-2C) and at least one flexible protective sleeve 40 (FIGS. 7A and 7B) supported by the retaining device 50 such that the at least one flexible protective sleeve can be inserted through a suprapatellar region SR (FIG. 12B) of the leg. The suprapatellar region SR as used herein means the region on the leg that is generally cranial to the patella P. Further, a rigid sleeve 30 can be at least partially disposed in the flexible protective sleeve 40. The rigid sleeve 30 is configured to receive therein canal preparation instrumentation for instance, a portion of a trocar 80, a drilling assembly and a reamer. A wire guide 90 (FIG. 6A) can also be disposed at least partially within the rigid sleeve 30 and is used to guide one or more wires 106 toward the bone T (FIG. 15). The wire 106 can guide canal preparation instrumentation toward the bone T, as further detailed below. The flexible sleeve 40 can flex as needed to accommodate a curved portions of the nail 300. Further, the flexible sleeve 40 is configured to protect tissue during the canal C preparation and nail 300 insertion phases, while the rigid sleeve 30 can protect the flexible sleeve 40 from the instrumentation disposed in the rigid sleeve 30.

Referring to FIG. 1, the system 1 can also include an insertion device 10 connectable to the intramedullary nail 300 and further configured to advance the intramedullary nail 300 along the superior-inferior direction S1 through the at least one flexible protective sleeve 40 and into the medullary canal C, for instance when the rigid sleeve 30 has been removed from the flexible sleeve 40. The system 1 also includes an aiming device 200 configured to guide one or more anchors 8 into the bone T and nail 300 along a transverse direction S2 or second direction that is generally transverse to the superior-inferior direction S1. It should be appreciated that the transverse direction S2 can be any radially aligned direction that is transverse to the superior-inferior direction S1. The aiming device 200 is configured to support a guide sleeve 60 such that guide sleeve 60 is positioned along the transverse direction S2 toward the bone T. The anchor 8 can be inserted through the guide sleeve 60 and fixed to the bone T, as shown in FIG. 1, and further detailed below. As should be appreciated, the guide sleeve 60 protects tissue during the intramedullary nail 300 fixation phases as further described below.

The system 1 as described herein may be used to insert nail through the suprapatellar region SR when the patient's knee is positioned between about 10 to 20 degree flexion. The knee flexed to between 10 and 20 degrees during nail 300 insertion can minimize possible bone fragment misalignment compared to the procedure where the knee is positioned at 90 degree flexion and the quadriceps muscles pulls the proximal bone fragment askew. The system 1, kit and method as described herein may be used to stabilize fractures in proximal tibia, distal tibia, and the tibial shaft, open and closed tibial shaft fractures, tibial malunions and nonunions, and certain pre- and postisthmic fractures, for example.

The system 1 may also include preparation instrumentation used to facilitate preparation of the medullary canal C for suprapatellar insertion of a nail 300 therein. For instance, preparation instrumentation may include a drill assembly (not shown) with a cannualated drill bit positioned distally on the drill assembly, wherein the cannualated drill bit is slidable along a guide wire 106 to prepare the canal C. A reamer (not shown) can be used as needed to further prepare the medullary canal C for receiving the intramedullary nail 300 therein, wherein reamer is cannualated so as to slidable along the wire 160 through the rigid sleeve 30 toward the bone canal C.

The system 1 may also include fixation and insertion instrumentation used to facilitate inserting the intramedullary nail 300 into the canal C. For instance, a cap and hammer assembly (not shown) can be used to advance the intramedullary nail 300 into the canal C. When the intramedullary nail 300 is in position, a bone drill assembly (not shown) can be disposed in the guide sleeve 60 to prepare the bone T for receiving the anchor 8. When the bone drill assembly is removed, the drive mechanism 70 and anchor 8 can be inserted into the guide sleeve 60.

Figure 2A:
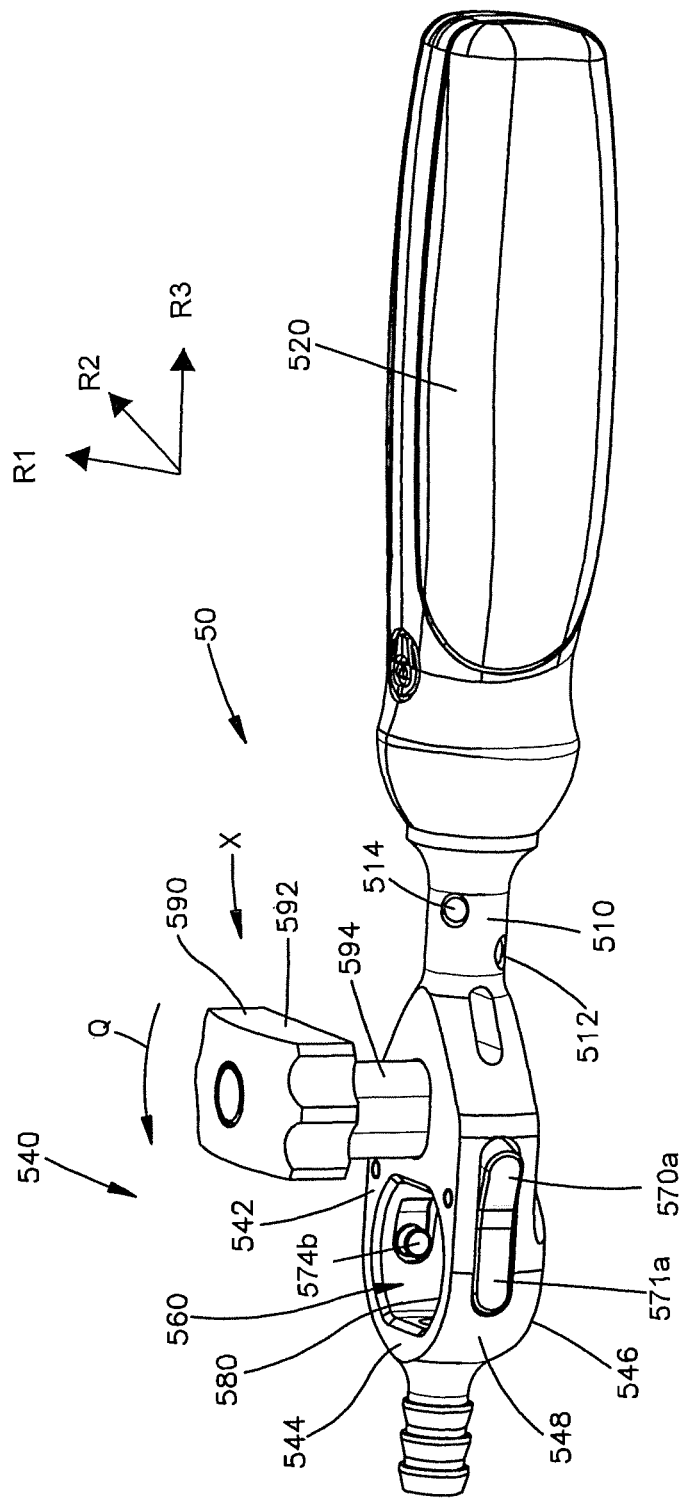
FIG. 2A is a perspective view of a retaining device used with the system shown in FIG. 1.

With reference to FIGS. 2A-2C, 7A and 7B, the retaining device 50 is configured to retain one or more sleeves 30, 40 therein. Further, the retaining device 50 is configured to position the respective sleeves at least partially in the leg such that the instrumentation, for instance, the trocar 80, insertion device 10 and nail 300, can be disposed through the sleeves 30 and 40 as needed. As shown in FIG. 2A, the retaining device 50 can include a retaining member 540 supported for instance, by a handle 520. The retaining member 540 is spaced apart from the handle 520 along a retaining device axis R3 or first retaining member axis R3. The handle 520 is configured to ergonomically receive a user's hand. For instance the handle 520 is shown elongate along the axis R3, but it should be appreciated the handle 520 can have any configuration, shape, geometry, or include any additional device or structure that can be held by a user.

Figure 7B:
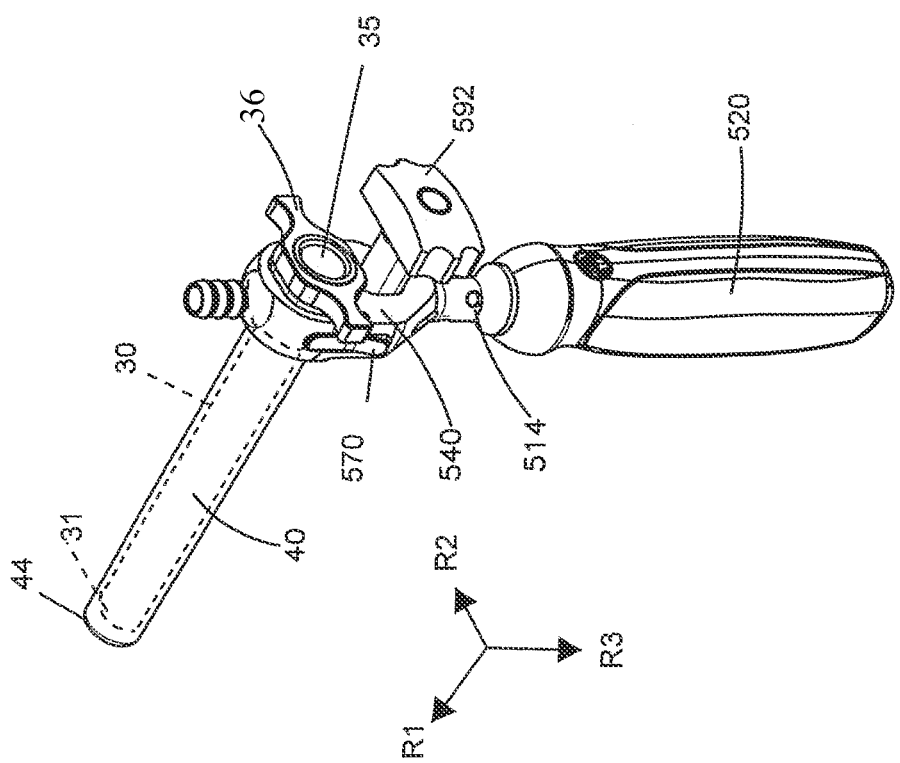

Continuing with FIGS. 2A-2C, 7A and 7B, the retaining member 540 is configured to hold at least the flexible sleeve 40. As discussed above, the rigid sleeve 30 can be inserted in the flexible sleeve cannulation 45 (FIGS. 7A and 7B). The retaining member 540 is also configured to fix the retaining device 50 in position on the patient's leg. The retaining member 540 defines a retaining body 542 connected to or for instance integral with an intermediate body 510. The intermediate body 510 can define one or more bores 512 and 514 extending transversely along axis R3 through the intermediate body 510. The one or more bores 512, 514 are configured to receive a fixation wire 107 (FIG. 17) therethrough that can fix the retaining device 50 in position relative to the leg. As shown in FIG. 17, the fixation wire 107 can define a distal end 107d. The distal end 107d can be inserted through either of the bores 512 or 514 to engage the femur F such that retaining device 50 is fixed in the desired position relative to the leg.

The retaining body 542 can also define an opening 560 sized to receive at least a portion of the flexible sleeve 40, and/or at least a portion of the rigid sleeve 30. The retaining body 542 defines a first surface 544, and a second surface 546 spaced apart from the first surface 544 along a retaining device transverse axis R1. The body 542 further defines a wall 548 at least partially connecting and extending between the first and second surfaces 544 and 546 along the retaining device transverse axis R1 The retaining body 542 can also define a circumferential channel 580 disposed in the opening 560 that is configured to receive a portion of the flexible sleeve 40.

The retaining member 540 can include at least one locking member 570a, 570b (two are shown) configured to selectively lock and unlock the flexible sleeve 40 and rigid sleeve 30 in the retaining device 50. The wall 548 can define at least one inner cavity (not shown) for supporting the locking member 571. The locking member 570 is shown positioned in the wall 548 of the retaining body 542. The locking member 570 defines a locking member body 571 and a projection 574a, b operably connected to the body 571a, b and extending through the wall cavity along a lateral retaining device axis R2, which is perpendicular to the axes R1 and R2. In an embodiment, the body 571a is configured to bias the projection 574a at least partially in to the opening 560. When the locking member 570a is depressed along the axis R2, the projection 574a is retracted within the wall 548, and the flexible sleeve 40 can be inserted into or pulled from the channel 580. When the locking member is 570 is released, the projection 574 is biased into the opening 580 such that the projection 574 can help prevent axial displacement of the flexible sleeve 40 along the axis R1.

The retaining member 540 can include a moveable blocking device 590 configured to selectively obstruct the opening 560, with can prevent possible axial displacement along the axis R1 of the rigid sleeve 30, flexible sleeve 40, and/or trocar 80. The blocking device 590 can define a base 594 supported for instance by the retaining body 542. The blocking device 590 can further include a blocking member 592 rotatably coupled to base 594 so that the blocking member 592 can move between a first position X shown in FIGS. 2A and 2B wherein the opening 560 is unobstructed by the blocking member 592, and a second position Y (shown in dashed lines in FIG. 2C) wherein the blocking member 592 at least partially obstructs the opening 560. The blocking member 592 can further define a surface 592b that faces the retaining body 542. The blocking member 592 is positioned on the base 594 so that the surface 592b is spaced apart from the retaining body 542 along the axis R1 a distance BD. The distance BD is defined as the distance between the surface 592b of the blocking member 592 and the surface 544 of the retaining body 542. The blocking member 592 is spaced apart from the surface 544 of the retaining body 542 such that when blocking member 592 is rotated in the direction Q (FIG. 2A), at least a portion of the blocking member 592 is in at least partial axial alignment along the axis R1 with the opening 560.

While a rotating blocking device 590 is shown in the figures and described above, the blocking device is not limited to such a configuration. In alternative embodiments for example, the blocking device 590 may be configured as a slidable member disposed on the base 594 and spaced apart from the retaining body surface 544. In such an embodiment the slidable member (not shown) is moveable from a first position wherein access to the opening 560 is unobstructed to a second position wherein the opening 560 is at least partially blocked by the slidable member. It should be appreciated that other blocking devices, mechanisms, and structures may be used well.

With reference to FIGS. 3A and 3B, the flexible sleeve 40 is configured to flex as need to accommodate insertion of the nail 300 therethrough. Further, the flexible sleeve 40 is configured to protect soft tissue while the tibial nail 300 is inserted into the medullary canal C of the bone T. Further, the flexible sleeve 40 is also configured to protect soft tissue while the medullary canal C is being prepared insertion of the intramedullary nail 300 therein, for instance when a drill bit is disposed in the flexible sleeve 40. The flexible sleeve 40 defines a trailing end 42, and a leading end 44 spaced apart from the trailing end 42 along a longitudinal axis P1, and body portion 41 extending between the leading and trailing ends 44, 42. The flexible sleeve 40 defines a longitudinal cannulation 45 extending along the longitudinal axis P1 between the trailing and leading ends 42, 44. The flexible sleeve defines an inner surface 49, which defines the cannulation 45. The trailing end 42 includes an outer rim 46 having first and second radial detents 47 and 48 disposed around the outer rim 46 in a diametrically opposed relation. The retaining member channel 580 also defines diametrically opposed protrusions 586 and 588 (FIG. 2C). The first and second radial detents 47 and 48 can receive the opposed protrusions 586 and 588 (FIG. 2C). In the illustrated embodiment, the cross-sectional dimension of the outer rim 46 is larger than the cross-sectional dimensional of any other portion of the body portion 41. The flexible sleeve 40 has a length such that when it is positioned within the knee K, the leading end 42 can extend to but not enter or penetrate the proximal end of bone.

The flexible sleeve cannulation 45 is sized to receive at least the intramedullary nail 300 and insertion member 11 therein. Specifically, the cannulation 45 defines a cross-sectional dimension 410 extending transverse to the axis P1 between opposing portions of the inner surface 49. When the intramedullary nail 300 is inserted through the longitudinal cannulation 45, the flexible sleeve 40 can bend or flex to accommodate any curved portion 12 of the intramedullary nail 300. The flexible sleeve 40 is configured to flex so as to change a shape of the first axis P1 from a first configuration to a second configuration, wherein the second configuration is different than the first configuration. The first configuration can be the configuration of the first axis P1 and flexible sleeve as shown in FIGS. 3A and 3B. The second configuration can be defined as when the axis P1 is curved, crimped, bent or twisted for instance, when the curved nail 300 is inserted in the sleeve cannulation 45 of the flexible sleeve 40.

The flexible sleeve 40 is formed of a soft, pliable, and flexible material so that the sleeve 40 can flex, bend, and/or contort when from the first configuration to the second configuration. Stated differently, the flexible sleeve 40 is designed to withstand, by flexing as needed, the rigors of medullary canal C preparation and also the insertion of the nail 300 therein. In an embodiment, the flexible sleeve 40 is made of a thermoplastic elastomer. An exemplary elastomer is an elastomer sold under the trademark Santoprene™ by Exxon Mobil Corporation. While an elastomer is preferred, other materials may be used as well. For example, the flexible sleeve 40 may be formed any polymeric material, including one or more polymers, and/or copolymer, polymer blend, or a composition of a polymers, co-polymers, additives and/or fillers that yield a soft, flexible and pliable material yet retain the structural integrity in use.

Referring to FIGS. 4A and 4B, a rigid sleeve 30 is shown that is configured to be at least partially inserted inside the flexible sleeve 40. The rigid sleeve 30 defines a leading end 31a trailing end 33 spaced apart from the leading end 31 along an axis P2, and a shaft 34 extending between the leading and trailing ends 31, 33. The rigid sleeve 30 defines a longitudinal cannulation 35 extending along the axis P2 through the shaft 34 and between the leading and trailing ends 31, 33. The longitudinal cannulation 35 is sized to receive at least a portion of a trocar 80 and/or the wire guide 90, as described above. Further, the cannulation 35 is sized to receive at least a portion of the drill bit (not shown) and reamer (not shown). The rigid sleeve 30 is elongate with a length selected for suprapatellar insertion. The shaft 34 defines and outer surface 131 and opposed inner surface 133. Further, the shaft 34 defines a rigid sleeve cross-sectional dimension 130 extending transverse to the axis P1 between opposing portions of the shaft outer surface 131. The rigid sleeve cross-sectional dimension 130 is less than or about equal to the flexible sleeve cannulation cross-sectional dimension 410, such that the shaft 34 can be inserted in the flexible sleeve cannulation 45. Further, the cannulation 35 defines rigid sleeve cannulation cross-sectional dimension 132 extending transverse to the axis P1 between opposing portions of the inner surface 133. The rigid sleeve 30 has a length so as to extend from at least an incision site 104 (FIG. 12B) to the proximal surface TP of the proximal tibia. The rigid sleeve 30 may be formed of steel, stainless steel, a stainless steel and/or metallic alloy, or any other durable, rigid, and biocompatible material. The rigid sleeve 30 protects the flexible sleeve 40 during the drilling and reaming operations discussed below.

Figure 8A:
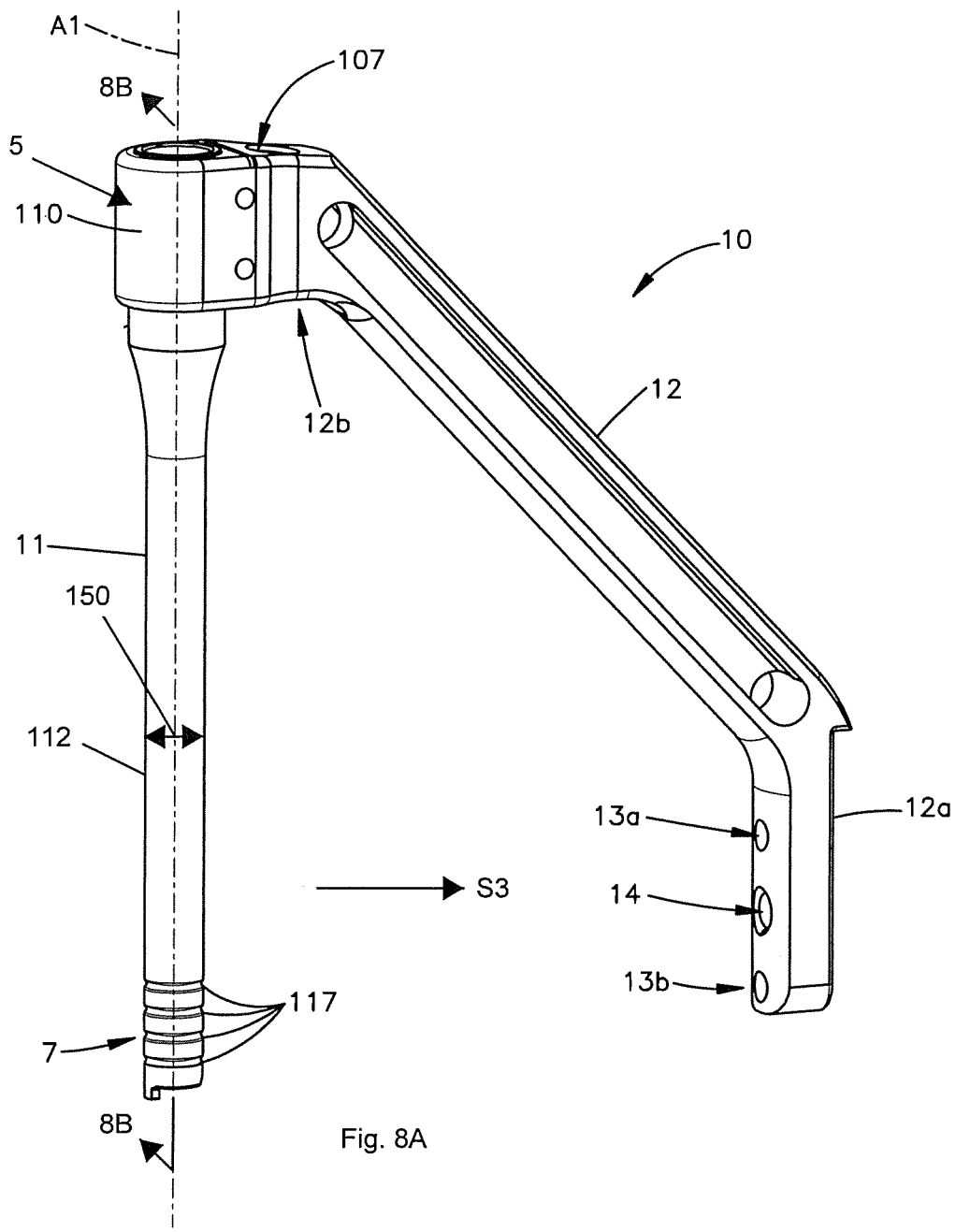
FIG. 8A is a perspective view of an insertion device of the system shown in FIG. 1.
Figure 8B:
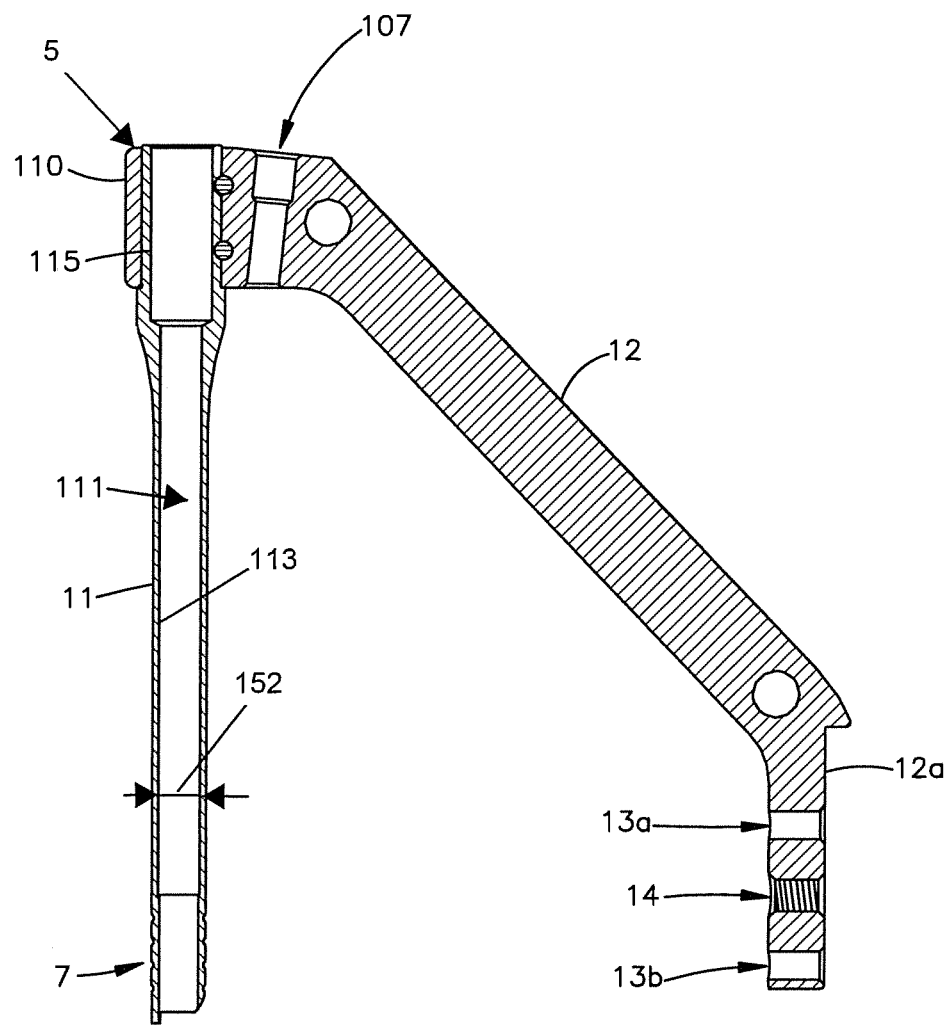
FIG. 8B is a sectional view of an insertion device of the system shown in FIG. 8A taken along lines 8B-8B.

The rigid sleeve 30 further defines an engagement member 36 disposed at the trailing end 33 of the sleeve 30 and configured to engage the retaining device 50. The engagement member 36 can define an engagement body 38 with a ridge 39 projecting radially outwardly from the shaft 34 in a direction that is transverse to the axis P2, and at least one finger 32 (a finger pair 32 is shown) extending radially outward from the engagement body 38. As illustrated, a cross-sectional dimension of the engagement member 36 that extends along a direction transverse to the rigid sleeve axis P2 is larger than the cross-sectional dimension of the shaft 34 and the distal end 31 of the rigid protective sleeve 30 such that when the rigid sleeve 30 is inserted into the flexible sleeve 40, the ridge 39 abuts a portion of the flexible sleeve 40 preventing further advancement of the rigid sleeve 30 through the flexible sleeve cannulation 45. The at least one finger 32 permits a user to remove the rigid sleeve 30 from the sleeve 40 by grasping finger 32 and pulling the rigid sleeve 30 out of the flexible sleeve 40. Further, the engagement body 38 can define at least one recess 37a, 37b that is configured to engage a portion of the retaining device 50. Specifically, the recess 37a and 37b are configured to receive corresponding projections 574a, 574b of the locking members 570a and 570b (FIGS. 2A-2C). When the locking members 570a and 570b are depressed by the user along axis R2, the projections 574a, 574b are retracted within the wall 548, and the rigid sleeve 30 can be inserted into the flexible sleeve cannulation 45 until the engagement member 36 is partially disposed within the retaining member opening 560, as shown in FIG. 8A. When the locking members 570a and 570b are released, the respective projections 574a and 574b are biased through the wall 548 into the opening 580 along the axis R2 and into engagement with engagement member recesses 37a and 37b respectively, further the locking the rigid sleeve 30 in position.

Turning to FIG. 5, the trocar 80 is configured to be at least partially disposed in the rigid sleeve 30. When trocar 80 is inserted in the rigid sleeve 30, the trocar 80, sleeves 30 and 40 can be supported by the retaining device 50 for positioning in the leg. The trocar 80 can be used to displace soft tissue in the suprapatellar region SR. The trocar 80 defines a trailing end 81, a leading end 83 spaced apart from the trailing end 81 along a trocar axis T1, and a shaft 86 disposed between the trailing and leading ends 81 and 83, respectively. The trocar 80 further defines a trocar engagement member 84 at the trocar trailing end 81 and a tapered tip 82 at the trocar leading end 83. The tip 82 and shaft 86 are sized for slidable engagement within the cannulation 35 of the rigid sleeve 30 such that the tip 82 protrudes from the leading ends 44 and 31 of the respective sleeve 40 and 30. The shaft 86 defines an outer surface 181. The shaft 86 further defines a rigid sleeve cross-sectional dimension 186 extending transverse to the axis T1 and between opposing portions of the outer surface 181. The trocar shaft cross-sectional dimension 186 is less than or about equal to the rigid sleeve cannulation cross-sectional dimension 332, such the shaft 86 cab be inserted in the rigid sleeve cannulation 35. Accordingly, the trocar 80 is configured for insertion in the cannulation 35 of the rigid sleeve 30 such that the tip 82 protrudes from the leading end 31 of the rigid sleeve 30 and the leading end 44 of the flexible sleeve 40. While the illustrated system 1 shows the trocar 80 inserted directly within the rigid sleeve 30, in other embodiments, the trocar 80 may be at least partially inserted directly within the cannulation 45 of the flexible sleeve 40.

The engagement member 84 of the trocar 80 is configured to engage at least a portion of the rigid sleeve 30 and/or the retaining device 50. The engagement member 84 may include a body 85 that forms a ridge 88 projecting radially outwardly from the shaft 86 in a direction that is transverse to the axis T1. When the trocar 80 inserted into the rigid sleeve 30, the ridge 88 abuts the engagement member 36 of the rigid sleeve 30, thereby preventing further advancement of the trocar 80 along the sleeve cannulation 35. Accordingly, the cross-sectional dimension of the enlarged member 84 is larger than the cross-sectional dimension of the shaft 86 and the tip 82. The body 85 further defines a channel 87 circumferentially disposed around the body 85, and is configured to facilitate manual manipulation by the surgeon. It should be appreciated that the body 85 can also define multiple grooves, flutes, holes, divots or knurls as needed.

The trocar tip 82 is configured to displace soft tissue in the area around and between the proximal bone TP and patella P. It should be appreciated that the tip 82 may have any shape, geometry, or include an additional structure or device that could displace soft tissue within the knee. For instance, the tip 82 can define a curved end, such as a hemispherical cap similar to that shown in FIG. 7. In other embodiments, the trocar tip 82 may have a wedge shape. Further, the degree of taper along the tip 82 may be varied as needed.

The trocar 80 may be formed of any biocompatible material, such as a polymeric material, metallic and/or alloy materials as needed. In a preferred embodiment, the trocar 80 may be formed of polyether ether ketone (PEEK). However, the system 1 is not limited to a PEEK trocar.

Referring to FIGS. 6A and 6B, the wire guide 90 is configured to be at least partially disposed in the rigid sleeve 30. The wire guide 90 is also further configured to guide one or more wires 106a, 106b (FIG. 15) toward a desired anatomical site when the wire guide 90 is disposed with the sleeves 30, 40 and the sleeves 30, 40 are supported by the retaining device 50 partially within the leg. The wire guide 90 is configured to guide a first wire 106a toward a first anatomical location, for instance the location on the proximal end of the bone T where the canal C is to be formed. If needed, a second wire 106b can be guided toward a more desirable second anatomical location while the wire guide 90 is disposed in the rigid sleeve 30 and the first wire 106a remains in the wire guide 90.

Continuing with FIGS. 6A and 6B, the wire guide 90 defines a proximal end 95, and a distal end 93 spaced apart from the proximal end 95 along a wire guide axis W1. The wire guide 90 can also define an elongate shaft 94 extending between the opposed proximal and distal ends 93 and 95 along the wire guide axis W1. The proximal end 95 of the wire guide 90 defines an enlarged member 96 configured to engage a portion of the rigid sleeve 30 when the wire guide 90 is disposed partially within the rigid sleeve 30. The distal end 93 of the wire guide 90 can define a tip 91. The shaft 94 and tip 91 are sized to be slidably received in the rigid sleeve cannulation 35, while the enlarged member body 98 engages the trailing end 33 of the rigid sleeve 30, preventing further advancement of the wire guide 90 through the rigid sleeve cannulation 35. The wire guide shaft 94 defines and outer surface 191. The shaft 94 further defines a cross-sectional dimension 194 that extends between opposing portion s of the shaft outer surface 191 and along a wire transverse direction WT that is transverse with respect to the axis W1. The wire guide cross-sectional dimension 194 is less than or about equal to the rigid sleeve cannulation cross-sectional dimension 132. The wire guide is thus configured to be slidable received in the rigid sleeve cannulation 45.

The enlarged member 96 defines a body 98 including a ridge 98a projecting radially outwardly from the shaft 94 in along the wire transverse direction WT. When the wire guide 90 is inserted into rigid sleeve 30, the ridge 98a can abut the engagement member 36 of the rigid sleeve 30. The enlarged member body 98 can define grip portions 94 that facilitate manipulation by the surgeon, for instance to rotate the wire guide 90 within the rigid sleeve 30 so as to reposition the wires 106 as needed.

The enlarged member body 98 can also define first and second bores 91 and 92, each of which are configured to receive the wires 106a or 106b (FIG. 15) therein. Each bore 91 and 92 can define a cross-sectional dimension extending along a wire transverse direction WT. The wires 106a, 106b can define a wire cross-sectional dimension. The cross-sectional dimensions of the bores 91 and 92 are larger than the cross-sectional dimensions of the wires 106a and 106b. The first bore 91 is disposed along the radial center C of the wire guide 90 and extends along the wire guide axis W1 toward the distal end 93. The tip 91 can define a first bore exit portion 92e. The second bore 92 is laterally offset a distance LD relative to the first bore 91. The wire guide shaft 94 can define a groove 92g (FIG. 6A) that extends along the shaft 94 toward the tip 91, and a bridge portion 97 that spans the groove 92g along the transverse direction WT. The second bore 92 extends through the enlarged member body 98 and is in open communication with the groove 92g at the body ridge 98a. The tip 91 can define a groove exit 92e.

Figures 9A, 9B:
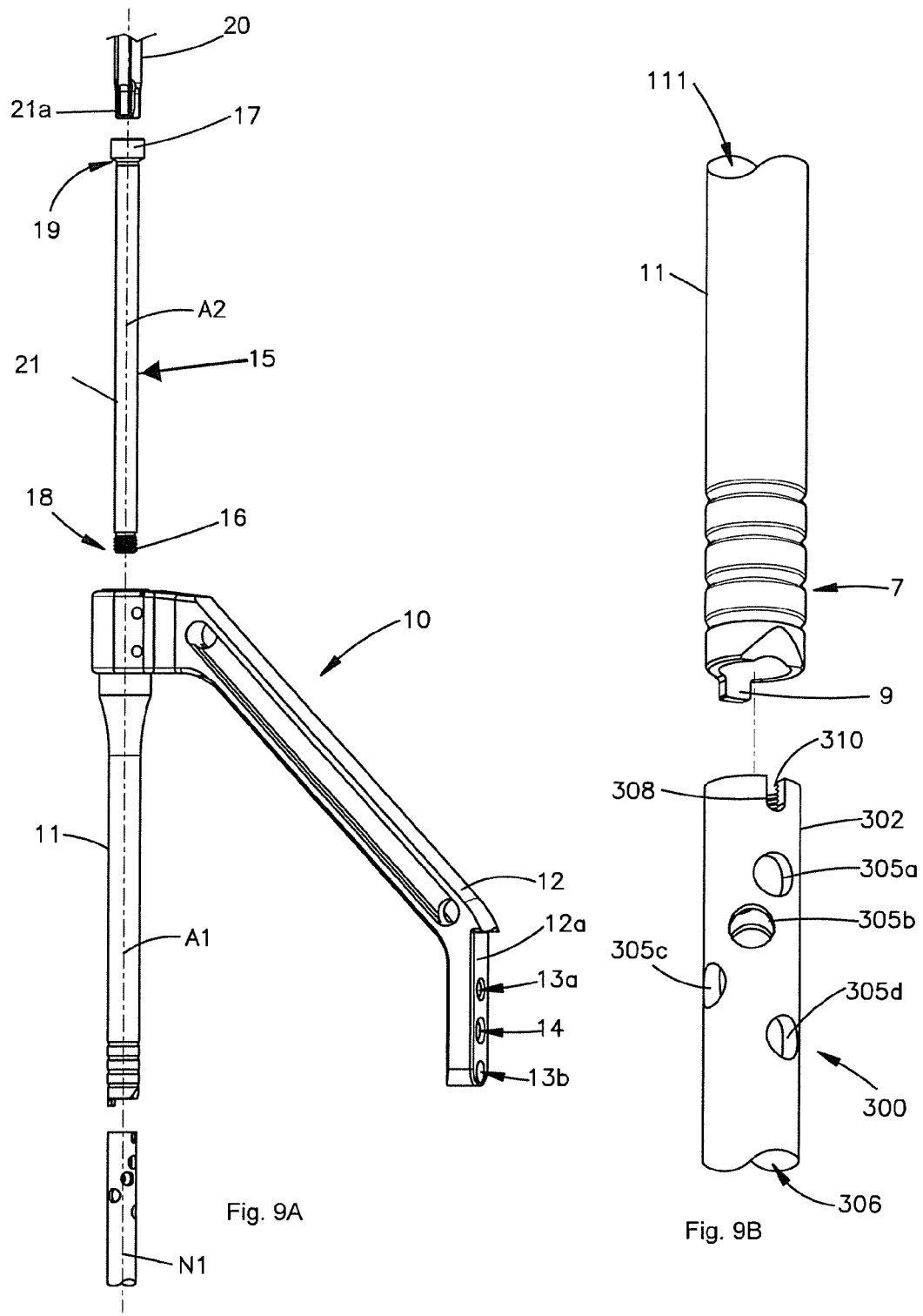
FIG. 9A is a perspective view of the insertion device shown in FIG. 2A illustrating a connection device, a drive mechanism, and a portion of an intramedullary nail.
FIG. 9B is an enlarged partial perspective view of the insertion device and a proximal end of the intramedullary nail shown in FIG. 10A.
Figure 9C:
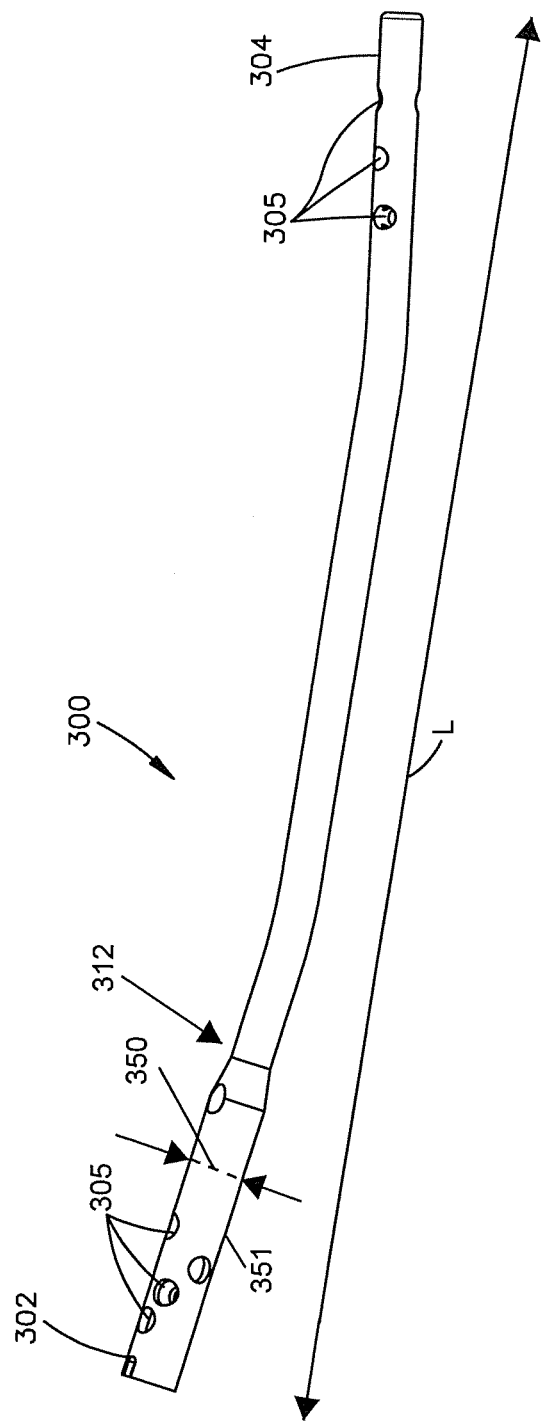
FIG. 9C is a perspective view an intramedullary nail shown in FIG. 9B.

Referring to FIGS. 9B and 9C, a nail 300 can include a proximal end 302 and a distal end 304 spaced apart from the proximal end 302 along a longitudinal direction L. The longitudinal direction L of the intramedullary nail 300 refers to the length direction the intramedullary nail 300. The intramedullary nail 300 defines a nail bore 306 extending at least partially between the proximal and distal nail ends along the longitudinal direction L. The intramedullary nail 300 also defines a plurality of openings 305 disposed at the distal and proximal ends of the intramedullary nail 300, respectively, and are configured receive one or more anchors 8. The intramedullary nail openings 305a, 305b, 305c, and 305d are positioned at different locations and orientations on the proximal end 302 of the intramedullary nail 300 so as to receive therein anchors 8. The distal end 304 can have similar openings 305. The intramedullary nail 300 may be elongate along the longitudinal direction L and can further define at least one curved portion 312 disposed between the proximal end 302 and the distal end 304. The curved portion 312 aligns the intramedullary nail 300 with the proximal tibia relative to the tibial shaft and/or the distal tibia and tibial shaft. The nail 300 also defines a cross-sectional dimension 350 that extend transversely to the longitudinal direction L of the nail 300.

The nail 300 can define a nail outer surface 351. The nail 300 can further define at least one cross-sectional dimension 350 extending between opposed portions the nail outer surface 351. The nail cross-sectional dimension 350 is less than or about equal to the flexible sleeve cannulation cross-sectional dimension 410. The nail 300 is thus configured to be slidable received in the flexible sleeve cannulation 45. It should be appreciated that the nail can have varying cross-section dimensions as illustrated in FIG. 9C. In alternate embodiments, the intramedullary nail 300 can be generally linear as needed for the particular fracture on or position within the bone T. It should be appreciated that any nail 300 may be used as described herein. Different sized nails 300 may be used, according the fracture location(s) and/or anatomical constraints. For example, the intramedullary nail 300 can have one more selected diameters, lengths, and or profiles, as needed.

Referring to FIGS. 8A through 9B, the insertion device 10 can include an insertion device body 110, an insertion member 11 extending from the insertion device body 110 along a insertion member axis A1, and a connecting arm 12 extending from the insertion member 11 and configured for connection to the aiming device 200. As illustrated in FIG. 2A, the insertion member 11 defines a trailing end 5, a leading end 7 spaced apart from the trailing end 5 along a the axis A1, and a cannulation 111 extending between the trailing and leading ends 5 and 7 along the axis A1. The trailing end 5 can define a leading end cannulation portion 115. The leading end 7 of the insertion member 11 can engage the intramedullary nail 300, as further detailed below and illustrated in FIGS. 9A-9C. The insertion member 11 defines an outer surface 112 and inner surface 113 that defines the cannulation 111. The insertion member 11 also defines a cross-sectional dimension 150 that extends between opposing portions of the insertion member outer surface 112 and is transverse to the axis A1. The insertion member cross-sectional dimension 150 is less than or about equal to the flexible sleeve cannulation cross-sectional dimension 410. The insertion member 11 also defines a cannulation cross-sectional dimension 152 that extends between opposing portions of the insertion member inner surface 113 and is transverse to the axis A1. The insertion member 11 is thus configured to receive in the cannulation 45 of the flexible sleeve 40. The insertion device body 110 also defines a secondary bore 107 that is offset from the axis A1. The secondary bore 107 is configured to receive therein at least portion of the cap and hammer assembly (not shown) that can be used to advance the intramedullary nail 300 along the superior-inferior direction S1. The insertion member 11 can include markings 117. The markings 117 on the insertion member 11 can be used to guide insertion depth of the intramedullary nail 300 in the canal C. The markings 117 are spaced a certain distance apart relative each other and also from the leading end 5 of the member 11 so that the intramedullary nail insertion depth can be gauged with reference to the position of the markings 17. The markings 117 can be radiographic and viewable via image analysis.

Turning to FIG. 9A, a connection device 15 can be used to connect the insertion device 10 to the intramedullary nail 300. The connection device 15, for instance an elongate rod 21, defines a proximal end 19, and a distal end 18 spaced apart from a proximal end 19 along a connecting device axis A2. The distal end 18 can define an engagement tip 16 configured to engage the intramedullary nail 300. The rod 21 and distal end 18 are sized to be slidably received by the insertion member cannulation 111. The rod 21 can also define a longitudinal bore 21b extending along the axis A2 between the proximal 19 and distal ends 19 and 18, respectively. When the connection device 15 is disposed in the insertion member cannulation 111, the distal end 18 of the connection device 15 protrudes from the leading end 7 of the insertion member 11 to engage the intramedullary nail bore 306. The intramedullary nail bore 306 further defines internal threads 310 (FIG. 9B). The engagement tip 16, which for instance is threaded, is configured to mate with the internal threads 310 of the intramedullary nail bore 306 so as to connect the intramedullary nail 300 and the insertion device 10. The proximal end 19 of the connection device defines a socket 17, for instance a hex socket. A drive mechanism 20 can be used to fix the connection device 15 to the intramedullary nail 300. The drive mechanism can define a distal tip 21a configured to engage the socket 17 of the connection device 15. To rotate the connection device 15, the surgeon can insert the tip 21a of a drive 20 into the socket 17 and then rotate the drive 20 to threadably secure the device 20 to the intramedullary nail 300. It should be appreciated that the socket 17 can have any configuration that can operably receive a distal end of a drive mechanism 20.

As shown in FIGS. 9A and 9B, the distal end 7 of the insertion member 11 is configured to engage the intramedullary nail 300. The distal end 7 of the insertion member 11 defines a protruding tab 9. The proximal end 302 of the intramedullary nail 300 defines at least one notch 308 (FIG. 9B). When the insertion member 11 is disposed on the intramedullary nail 300, the protruding tab 9 is received within the notch 8 so as to rotatably fix the insertion device 10 relative to the intramedullary nail 300. During use, the surgeon can insert the tab 9 of the insertion device 10 into the notch 308. Then, the surgeon can insert the connection device 15 into the cannulation 111 of the insertion member 11. Next, the connection device 15 is rotated (via the drive 20) relative to the insertion member 11 such that the threaded tip 16 mates with the internal threads 310 of the intramedullary nail bore 306 thereby coupling the intramedullary nail 300 to the insertion device 10.

Referring now to FIGS. 8A-9A, the connecting arm 12 is configured to attach to the aiming device 200. The connecting arm 12 defines a body portion 12b and a connection member 12a spaced apart from the body portion 12b along the axis A1. The connecting arm 12 is offset relative to the insertion member 11 such that the connection member 12a is spaced apart from the distal end 7 of the insertion member 11 along a direction S3 that is transverse to the axis A1. The direction S3 can be the same as the transverse direction S2 when the insertion device 10 is attached to the aiming device 200. The connection member 12a defines one or more (at least two 13a, 13b) alignment holes 13, and an internally threaded bore 14. The alignment holes 13a, 13b and threaded bore 14 are configured to receive portions of the aiming device 200. When the insertion device 10 is 1) positioned such that the intramedullary nail 300 is disposed in the medullary canal C, and 2) the insertion device 10 is connected to the aiming device 200 by the connecting arm 12a, the aiming device 200 is aligned relative to the intramedullary nail 300 so that an anchor 8 is insertable into one of the intramedullary nail openings 305.

Figure 10:
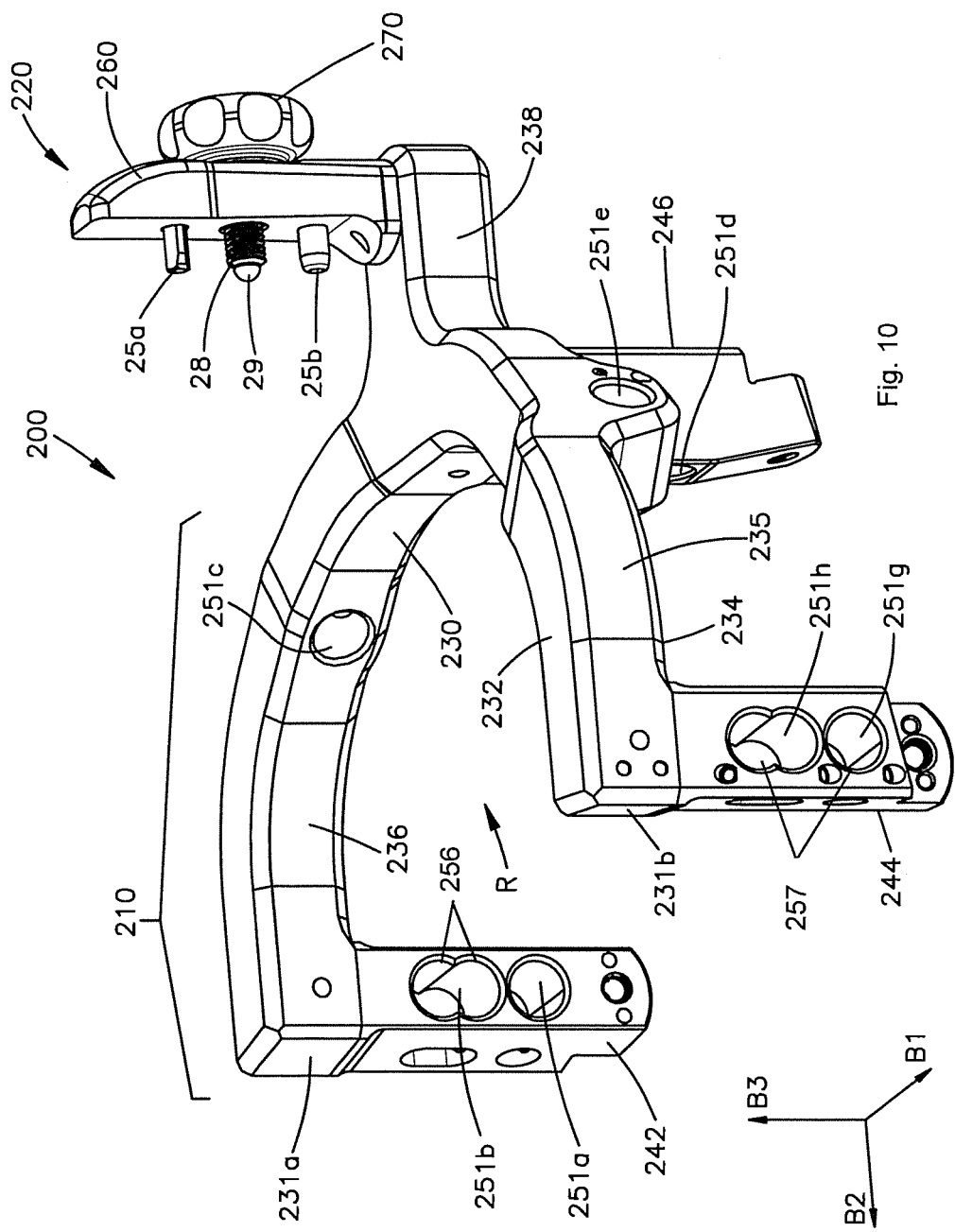
FIG. 10 is a perspective view of an aiming device of the system shown in FIG. 1.

With reference to FIG. 10, the aiming device 200 may include an aiming member 210 configured to guide at least one anchor toward the bone T and nail 300, and an attachment member 220 configured for connection to the insertion device 10. The aiming member 210 defines an aiming body 230 that is configured to support at least one guide sleeve 60 whereby the guide sleeve 60 is configured to guide the anchors 8 toward the intramedullary nail 300. The aiming member 210 can support, for instance fixedly support, a plurality of extension members 242, 244, and 246 that extend perpendicularly with respect to the aiming body 230. The extensions are configured to guide anchors into the bone T and nail 300.

In the illustrated embodiment, the aiming body 230 defines positioned between a first end 231a and a second end 231b spaced apart from the first end 231a along a first transverse axis B1, and an apex portion 238 positioned between the first and second ends. The aiming body 230 can define a region R within which a portion of the patient's leg is received. The region R can be defined along the first transverse axis B1 that is perpendicular to a second transverse axis B2 that extends generally from the apex portion 238 into a patient's leg when the system is positioned on the patient, and a third transverse axis B3 that extends along the superior-inferior direction SR and is perpendicular to the first and second transverse axes B1 and B2. The aiming body 230 defines a superior side 232, an inferior side 234 spaced apart from the superior side 232 along the third axis B3. The aiming body further defines an exterior wall 235 extending between the superior and inferior sides 232, 234, and an interior wall 236 configured to face the leg and extending between the superior and inferior sides 232, 234. The extension members 242, 244, and 246 extend from the aiming body 230 along the axis B3. In the embodiment shown in FIG. 10, the extensions 242, 244, and 246 protrude from the inferior surface 234 of the body 230. In alternative embodiments, the extensions 242, 244, and 246 may project from or be attached to any side or portion of the aiming body 230.

The aiming body 230 defines a plurality of channels 251a-h configured to at least partially receive and support either of a guide sleeve 60 (FIG. 1), at least one anchor 8, a drilling assembly, or a drive mechanism 70. As illustrated in FIG. 10, channels 251c and 251f are disposed in the aiming body 230, channels 251a and 251b are disposed in extension member 242, channels 251d and 251e are disposed in extension member 246, and channels 251g and 251h are disposed in extension member 244. Each of the plurality of channels 251 extend through the aiming body 230 along a transverse direction S2 and form a passage through which the guide sleeve 60 may be inserted through. In accordance with the illustrated embodiment, the inner surface (not numbered) of each channel 251 is configured to slidably receive the guide sleeve 60 (FIG. 10). Specifically, each channel 251 is configured such that when 1) the aiming device 200 is attached the insertion device 10, and 2) the intramedullary nail 300 is positioned in the canal C, at least one channel 251 is aligned with a direction that is transverse to the intramedullary nail 300 and aligned with an opening 305 on the intramedullary nail 300. Further, each channel 251 may be configured such that the guide sleeve 60 is manipulated within the channel 251 so as to align the distal end 61 of the guide sleeve 60 to the appropriate nail opening 305. One or more of the channels 251 can define elongate entry 257 and exit portions 256 when the channels are too close to each other to permit non-biased positioning of the instrumentation, such as the guide sleeve 60 and/or anchor 8. For instance, channel 251b may define an elongate exit portion 256 facing the region R that allows for biased positioning of a guide sleeve 60 and anchor 8. The channel 251b is biased or tapered from the exit portion 257 toward the opposed entry portion (not shown) along the axis B1. The channel 251b and exit portion 257 configuration allows controlled displacement of bony fragments, provides contact and apposition under patient weight bearing. Further, channel 251h can include an elongate entry portion 257 configured to allow for biased positioning of instrumentation therein. The channel 251h is biased or tapered from the entry portion 257 toward the opposed exit portion (not shown) along the axis B1.

While the aiming body 230 and extensions 242, 244 and 246 are described separately above, in alternative embodiments, the aiming body 230 and one or more of the extensions 242, 244 and 246 may be integrally formed. Further, aiming body 240, for instance can be a curved frame configured to support a guide sleeve. In still other embodiments, the curved frame is configured to support one or more extension members 242, 244 and 246, and the attachment member 220, wherein the extension members are configured to support the guide sleeve 60.

Continuing with FIG. 10, the attachment member 220 is configured to connect the aiming device 200 to the insertion device 10. The attachment member 220 includes an attachment body 260, at least one (a pair 25 is shown) alignment pin 25, and a securing device 270, wherein the alignment pin 25 and the portion of the securing device extend from the attachment body 260 along the axis B2. The attachment body 260 defines a bore (not numbered) that is sized to receive a portion of the securing device 270. The alignment pins 25a and 25b are configured to be inserted into the corresponding alignment holes 13a and 13b of the connection member 12a (FIG. 1). The securing device 270 defines a knob coupled to an externally threaded shaft 28 with a free end 29 that extends through the attachment body 260. The free end 29 of the threaded shaft 28 can extend into and through an attachment body bore (not numbered) to mate with the corresponding threaded bore 14 on the connection member 12a. The aiming device 200 may be connected to the insertion device 10 by inserting the threaded shaft 28 into threaded bore 14, while positioning the alignment pins 25 in the alignment holes 13 of the connection member 12a. The knob 270 may be rotated so that the threads of the shaft 28 mate with and engage the internal threads of the bore 14, thereby securing the attachment body 260 to the connection member 12a. It should be appreciated that the position of nail 300, insertion device 10, and aiming device 200 can be manipulated as needed to facilitate alignment. For example, the surgeon can, via radiographic image analysis confirm the position of the intramedullary nail 300 in the tibial canal C.

While a knob 270 and threaded shaft 28 assembly is shown, other securing devices may be used to fix the aiming device 200 to the insertion device 10. In an alternative embodiment, the securing device may be a clamp assembly configured to clamp the attachment body 260 to the connection member 12a. In other alternative embodiments, the securing device 25 can also be an interlock device that snaps-fits the attachment body 260 and connection member 12a together. Further, in other exemplary embodiments, the attachment body 260 may be a cylindrical body having an internally threaded bore, while the connection member 12a has externally disposed threads configured to engage the threaded bore. Such a configuration can couple the connection member 12a to the attachment body 260, thereby connecting the insertion device 10 to the aiming device 200. In any of the alternative embodiments described above, provision may be made to ensure proper alignment of the insertion device 10 relative to the aiming device 200, such as alignment pins, alignment tangs or detents, alignment shoulders, and visual indicators (e.g. color coding) to indicate proper alignment.

Referring now to FIGS. 11A and 11B, the guide sleeve 60 is configured to guide at least an anchor toward the intramedullary nail 300 when the guide sleeve 60 is supported by the aiming device 200. The guide sleeve 60 includes a distal end 62, a proximal end 64 spaced apart from the distal end 62 along an axis G1, and a shaft 66 extending between opposing proximal 64 and distal ends 62 and along the axis G1. The shaft 66 defines a guide sleeve cannulation 69 extending along the axis G1. The distal end 62 may be tapered. The proximal end 64 includes an engagement member 65 forming a ridge 68 extending from the shaft 66 along a direction that is perpendicular to the axis G1. The ridge 68 is configured to abut an outer surface of the aiming member 210 when the guide sleeve 60 is supported by the channel 251. It should be appreciated that when 1) the intramedullary nail 300 is disposed in medullary canal C, 2) the aiming device 200 is connected to the insertion device 10, and 3) the guide sleeve 60 is supported by the aiming device 200, the anchor 8 is insertable through the guide sleeve 60 into engagement with the bone T and into the corresponding opening 305 in the intramedullary nail 300.

When the anchor is inserted through the guide sleeve 60, a drive mechanism can be used to secure the anchor 8 to the intramedullary nail 300 and bone T. The drive mechanism 70 can include distal end spaced apart from the handle along a shaft portion. The distal end and shaft portions can be inserted through the guide sleeve cannulation 69 such that the drive distal end engages the anchor 8. The drive mechanism 70 can be rotated so as to fix the anchor 8 into the opening 305 of the intramedullary nail 300 and the bone T. It should be appreciated that other instrumentation may be inserted into the guide sleeve 60 as needed. For instance, a trocar may be inserted through the guide sleeve 60 to displace soft tissue proximate the cortex of the bone T. A portion of a bone drilling assembly may be inserted through the guide sleeve cannulation 69 to drill an opening in the bone to provide access to the intramedullary nail 300. One or more protective sleeves can be inserted into the guide sleeve cannulation 69.

The system can also include an extraction member (not shown) configured to be least partially inserted in the cannulation 111 of the insertion member 11 for operable connection the intramedullary nail 300 disposed in the medullary canal C. The extraction member may be connected to the intramedullary nail 300, locked in position and then pulled in a superior direction A so as to remove the intramedullary nail 300 from the bone T.

Referring generally to FIGS. 1 and 12-17, the system 1 may be used to implant a nail 300 in a medullary canal C of the bone T. Suprapatellar insertion, as discussed above, is insertion of the intramedullary nail 300 through a suprapatellar region SR of the leg as shown in FIG. 12A. To prepare for suprapatellar insertion and subsequent fixation of the intramedullary nail 300 to the bone T, the patient is placed in a supine position on a radiolucent table. While placing the patient on the radiolucent table, the knee K of the injured leg may be positioned on top of a knee roll 101 to ensure that knee K of the injured leg can be bent between an angle θ1 equal to about zero (0) degrees (full extension), and a flexion angle θ2 that is between about 10 to 20 degrees. Angles θ1, θ2 are defined between a femur axis F1 and a tibia axis TB1 as shown in FIG. 12A. During certain steps of the method as disclosed herein, the injured leg is positioned at full extension to define an angle θ1 of about 0 (zero) degrees, while in other steps the knee K is flexed. The leg can define a superior direction A and an inferior direction I. The directions A and I align with the direction S1 discussed above.

Figure 13:
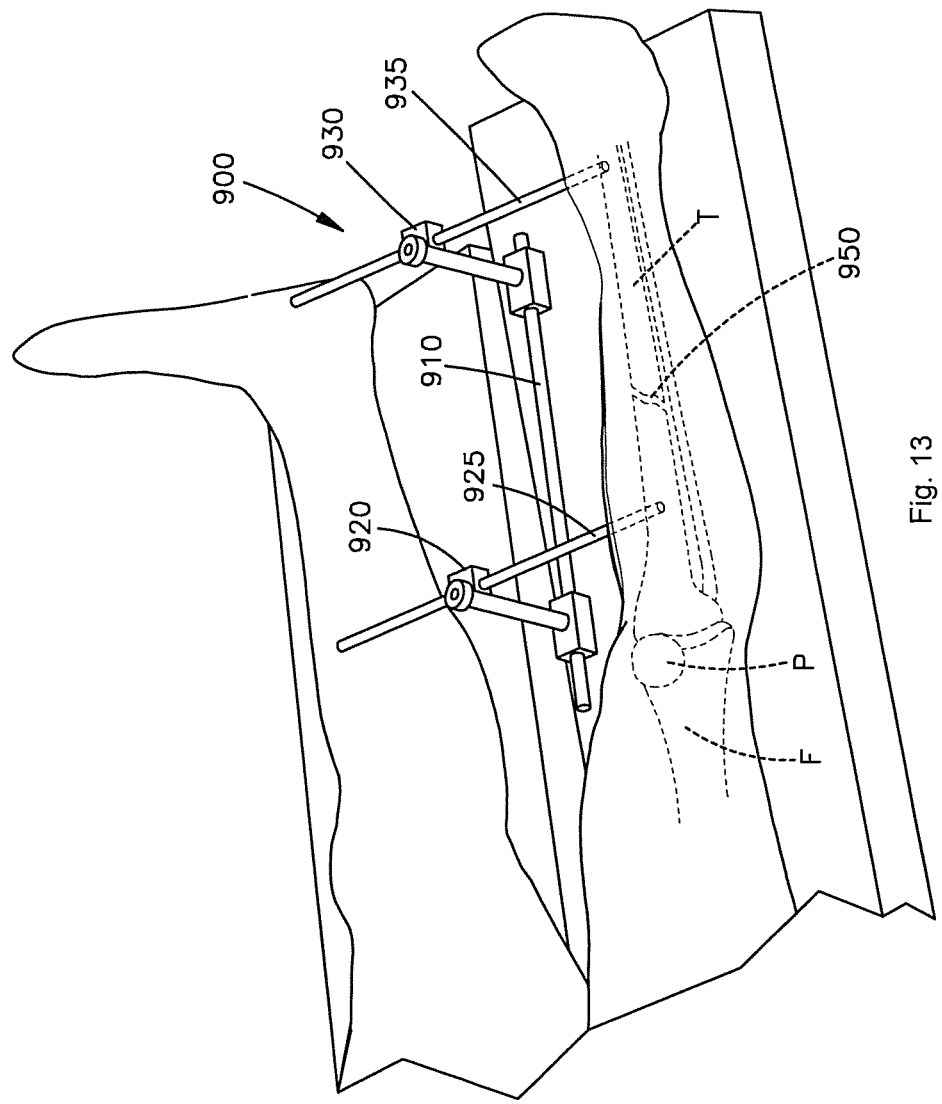
FIG. 13 illustrates an exemplary distractor used to reduce a fracture in a tibia in accordance with an embodiment of the present disclosure.

Turning to FIG. 13, initially the fracture 950 can be reduced to restore the fractured bone to its correct alignment. A distractor 900 depicted in FIG. 13 may be used to reduce the fracture, although any suitable distractor may be used. The distractor 900 can include two spaced parts rods 925 and 935 positioned in the bone T on opposing sides of the fracture 950. The rods can be secured to the respective clamps 920 and 930, and the spacing between the clamps 920 and 930, and thus rods 925 and 935 are decreased or increased as needed.

The surgeon can determine and identify the appropriate nail 300 length after reduction of the fracture 950. In an embodiment, the surgeon can use a radiographic ruler (not shown) that can be placed along the injured leg parallel to the bone T. The radiographic ruler is adjusted until its distal tip is at the level of the physical scar or the desired nail insertion depth. The surgeon then takes a radiographic image of the tibia and the ruler. The intramedullary nail length may be read directly from the ruler image, selecting the measurement at or just below the level of the anterior edge of the tibial plateau.

Next, the knee K may be positioned at or near full extension (θ1~zero degrees) while the incisions 104 is made in suprapatellar region SR, as shown in FIG. 12B. The incision 104 can be made closer to or further from the patella P as needed, depending on anatomical and other indications. A deep longitudinal incision (not shown) is made to split the quadriceps tendon in its midsubstance, just above its insertion into the patella P.

Following the reduction and incision steps, the method proceeds generally by next preparing the medullary canal C for insertion of the intramedullary nail 300 therein, followed by insertion and fixation of the intramedullary nail 300 to the bone T. Accordingly, after the incision 104 is made, the preparation assembly 105 is assembled and inserted through the incision toward the proximal tibia. Specifically, flexible sleeve 40 in inserted into and retained by the retaining device 50 as described above. The locking members 570 on the retaining member 540, for instance can be depressed so as to permit the flexible sleeve 40 to fit in the opening 560 and be received by the opening channel 580, as discussed above. The locking members 570 remained depressed so as retract the projections 574 within the wall 548, and then rigid sleeve 30 is inserted into the flexible sleeve 40. When the locking members 570a and 570b are released, the projections 574a and 574b engage the recesses 37a and 37b of the rigid sleeve engagement member 36 (FIG. 7A). Next, the trocar 80 is then positioned within the rigid sleeve 30 such that the tip 83 and a least a portion of the shaft 86 (not shown) protrudes from the leading ends 44 and 31 of the flexible sleeve 40 and the rigid sleeve 30, respectively. As discussed above, the retaining device 50 thus holds the rigid sleeve 30, the flexible sleeve 40, and the trocar 80 together. Next the blocking member 590 can be positioned a in blocking position Y (FIG. 2C) to block axial displacement along the axis R1 of the rigid sleeve 30 and trocar 80.

Using the retaining device 50, the flexible sleeve, the rigid sleeve 30, and the trocar 80, is inserted through the incision 104 and is advanced along an inferior direction I between the articular surface of the patella P and the trochlea of the distal femur. Neither the rigid sleeve 30 nor the flexible sleeve 40 penetrates the proximal portion of the bone T. however. During the insertion step the assembly 105, the patella P is displaced anteriorly. With the knee K at extension, the assembly 105 is advanced toward the tibia until the trocar 80 reaches the proximal surface of the tibia. As needed the surgeon can the reposition the blocking member 590 as needed unblocking position. Then, the trocar 80 is withdrawn in a superior direction A from the assembly 105 and patient.

Figure 14:
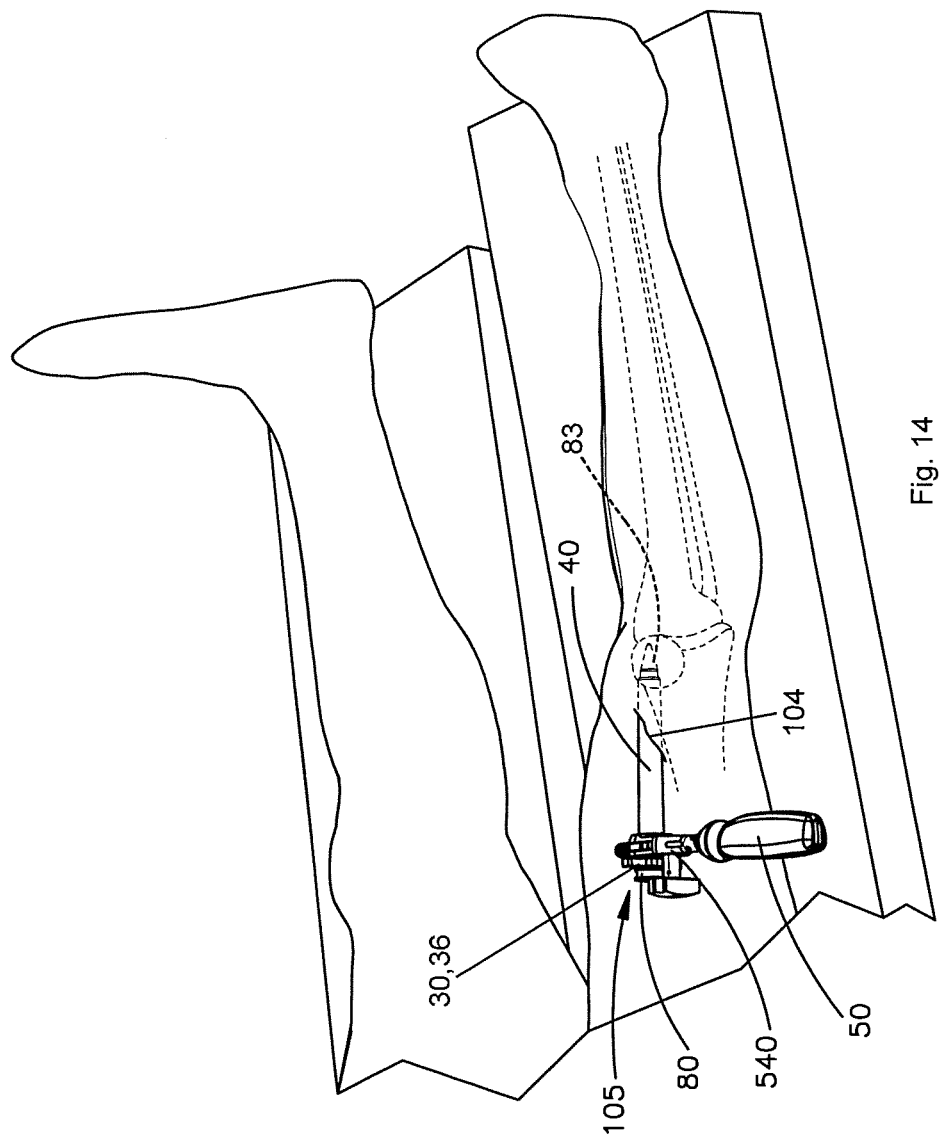
FIG. 14 illustrates the retaining device supporting the flexible sleeve, a rigid sleeve partially within the flexible sleeve, and a trocar partially within the rigid sleeve, and positioned in the leg such that the trocar tip engages the proximal end of the tibia, in accordance with an embodiment of the present disclosure.

With reference to FIG. 14, next the wire guide 90 is inserted into the rigid sleeve 30. The wire guide 90 is then advanced toward the anterior surface of the tibia T along the inferior direction I. As this point in the procedure, the knee K is flexed between 10 and 20 degrees to provide a radiographic location for a starting point and insertion of the wires 106a and 106b. The wires can be then aligned with the desired anatomical location. It should be appreciated that the wires 106a, 106b can include a distal end 106d, and a proximal end 106p spaced apart from the distal end 160d. The first wire 106a is then inserted through the first bore 91 of the wire guide 90. The wire 106a is then advanced to access the medullary canal C of the bone T. A radiographic image is taken to verify the position of the first wire 106a. If the wire 106a is positioned incorrectly, a second wire 106b may be inserted through the second bore 92, along the groove 92g toward the wire guide tip 91, while the first wire 106a remains in place in the first bore 92. The wire guide 90 may be then rotated within the rigid sleeve 30 to position the second wire 106b at the desired location. The first wire 106a can then be removed from the wire guide 90 if the second wire 106b is positioned appropriately. When the wire 106a or 106b is in the desired position, the wire proximal end 106p can be inserted into through the cannualated drill bit to guide the cannualated drill bit toward the bone T for forming the canal C. The cannualated reamer can be disposed along the wire 106 as needed. The system 1 can include multiple wire guides configured for the appropriate surgical method, for instance the wire guides can have multiple cross-sectional dimensions and lengths as needed for the particular leg anatomy.

With reference to FIG. 15, the retaining device 50 is subsequently anchored to maintain the position of the retaining device 50 during the procedure. The fixing wire 107 is inserted through the transverse bore 512 in the intermediate body 510 of the retaining device 50. The wire 107 is advanced until its distal tip 107d penetrates the patient's femur F. With the retaining device 50 fixed in position relative to the leg, a drilling assembly is used to prepare the canal C. The drilling assembly can include cannualated drill bit that can slide along the wire 106. The drill bit can placed over the wire 106 and is then advanced through the rigid sleeve 30 until the drill bit reaches the bone T. The drill assembly is then used to open the medullary canal C. If necessary, a cannualated reamer may slide along the wire 106 and used to enlarge the medullary canal C. After opening the medullary canal C, the drill bit and the wire 106, wire guide 90 and rigid sleeve 30 are removed from the patient. With the medullary canal C prepared, the steps used to insert and fix the intramedullary nail 300 to the bone T will now be described.

The insertion device 10 may be coupled to the intramedullary nail 300 as described above with respect to FIGS. 9A-9C. The rigid sleeve 30 is removed from the retaining device 50 and the flexible sleeve 40. With reference to FIG. 17, using the insertion device 10, the intramedullary nail 300 is inserted into the medullary canal C of the bone T through the flexible sleeve 40. If needed, a hammer assembly and cap can disposed in the bore 107 of body 110 and used to forcibly advance the intramedullary nail 300 into the medullary canal C. The appropriate position of the intramedullary nail 300 can determined by using radiographic imaging to determine the location of the markings 117 on the leading end 7 of the insertion member 11, as discussed above. Further, the position of the distal end 304 in the medullary canal C may be determined using radiographic imaging or other means.

With reference to FIG. 1, when the intramedullary nail 300 is positioned appropriately in the medullary canal C, the aiming device 200 is connected to the insertion device 10. The alignment pins 25 are positioned inside the bores 13 of the connection member 12a, while the securing device 27 secures the attachment body 260 to the connection member 12a, thereby aligning the at least one channel 251 with at least one opening 305 of the intramedullary nail 300. Preferably, one or more channels 251 are aligned with one or more corresponding openings 305. A guide sleeve 60 may then be inserted through the channel 251 of the aiming device 200 as shown in FIG. 1. Next, a portion of the bone drill assembly is positioned within the cannulation 69 of guide sleeve 60. The drilling assembly forms an opening in the bone T at a location proximate the opening 305 aligned with the selected channel 251. The drill assembly is then removed from the guide sleeve 60. Next, an anchor 8 is positioned on the distal end of the drive mechanism 70, and the anchor 8 and drive mechanism 70 are inserted into cannulation 69 of the guide sleeve 60. The drive mechanism 70 is use to rotate the anchor 8 so that anchor 8 engages the opening 305 of the intramedullary nail 300 thereby fixing the intramedullary nail 300 in the bone T. Additional anchors 8 can be positioned and fixed to the intramedullary nail 300 as needed.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed:

1. A system for inserting and securing, through a suprapatellar region of a leg, an intramedullary nail into a medullary canal of a bone, the system comprising:
    a flexible sleeve configured to be partially inserted in the leg, the flexible sleeve defining a leading end and a trailing end spaced apart from the leading end in a proximal direction along a first axis, the flexible sleeve defining a first cannulation extending along the first axis between the leading and trailing ends, the first cannulation sized to receive therethrough at least the intramedullary nail, wherein the flexible sleeve is configured to flex so as to change a shape of the first axis from a first configuration to a second configuration, wherein the second configuration is different than the first configuration;
    a rigid inner sleeve comprising a distal end, a trailing portion and an elongated shaft portion located between the distal end and the trailing portion;
    a retaining device comprising a handle and a retaining member that extends from the handle, the retaining member configured to releasably lock to the trailing end of the flexible sleeve, the retaining device further configured to releasably lock to the trailing portion of the rigid inner sleeve while the elongated shaft portion is disposed within the first cannulation of the flexible sleeve such that the flexible sleeve and the rigid inner sleeve are prevented from movement with respect to the retaining member along the first axis both in the proximal direction and in a distal direction opposite the proximal direction, wherein the retaining member is configured to position the flexible sleeve through the suprapatellar region of the leg such that the flexible sleeve leading end is aligned with a proximal end of the bone,
    wherein the intramedullary nail is insertable through the flexible sleeve and into the medullary canal.

2. The system of claim 1, further comprising an intramedullary nail, wherein the intramedullary nail defines a proximal end and a distal end, and at least one curved portion that is disposed at least between the proximal and distal ends of the intramedullary nail, and the flexible sleeve is configured to flex as the nail is inserted from the trailing end to the leading end.

3. The system of claim 2, wherein the retaining member comprises an upper surface and an opposed lower surface and an aperture extending from the upper surface to the lower surface where the aperture defines a center axis extending from the upper surface to the lower surface along a first direction, wherein the system further comprises an insertion device configured for removable connection to the intramedullary nail, wherein the intramedullary nail and at least a portion of the insertion device is configured to be received within the first cannulation of the flexible sleeve, wherein when 1) the insertion device is connected to the intramedullary nail, and 2) the flexible sleeve is inserted at least partially in the leg, the insertion device can advance the intramedullary nail through the flexible sleeve along the first direction to position the intramedullary nail in the medullary canal.

4. The system of claim 3, further comprising an aiming device connectable to the insertion device, the aiming device configured to guide at least one anchor toward the bone, wherein when 1) the aiming device is connected to the insertion device, and 2) the intramedullary nail is positioned in the medullary canal, the aiming device guides the at least one anchor toward the bone along a second direction that is transverse to the first direction.

5. The system of claim 4, wherein the insertion device further comprises an insertion member defining a leading end and a trailing end spaced apart from a leading end along a second axis, the insertion member defines an insertion member bore extending between the leading and trailing ends along the second axis, wherein the insertion member is configured to be at least partially disposed in the first cannulation of the flexible sleeve.

6. The system of claim 5, wherein the intramedullary nail defines a nail bore extending at least partially between the proximal and distal ends along a intramedullary nail direction, and one or more openings each configured to receive a portion of the at least one anchor, and the system further comprises a connecting rod configured to couple the insertion device to the intramedullary nail, wherein the connecting rod is configured to be at least partially disposed in the bore of the insertion member, wherein when the connecting rod is disposed at least partially in the bore of the insertion member, a portion of the connecting rod engages at least a portion of the intramedullary nail bore to connect the intramedullary nail to the insertion device.

7. The system of claim 5, wherein the proximal end of the intramedullary nail defines a notch, and the leading end of the insertion member defines a tab, wherein the tab is configured to be received by the notch so as to rotatably fix in the insertion member relative the intramedullary nail.

8. The system of claim 4, wherein the aiming device comprises an aiming member, and wherein the system further comprises a guide sleeve configured to be supported by the aiming member, wherein the guide sleeve defines a proximal end, a distal end spaced apart from an proximal end along a guide sleeve axis, and a guide sleeve cannulation extending between the proximal and distal ends along the guide sleeve axis, wherein the at least one anchor is insertable through the guide sleeve cannulation.

9. The system of claim 8, wherein the aiming member defines a first surface, a second surface spaced apart from the first surface along the second direction, and a plurality of channels extending between the first and second surfaces along the second direction, each channel configured to at least partially receive the guide sleeve therein.

10. The system of claim 9, wherein the aiming member is a frame that supports at least one extension member, the at least one extension member includes at least one of the plurality of channels, wherein when the aiming member is attached to the insertion device 1) the frame partially surrounds a portion of the leg, and 2) the at least one extension member extends along the first direction.

11. The system of claim 1, wherein the retaining member comprises an upper surface and an opposed lower surface and an aperture extending from the upper surface to the lower surface and the trailing end of the flexible sleeve is configured to releasably lock to the retaining member within the aperture of the retaining member and the trailing portion of the rigid inner sleeve is configured to releasably lock to the retaining member within the aperture of the retaining member.

12. The system of claim 11, further comprising a rotating blocking device located on the retaining member where the rotating blocking device comprises a shaft extending from the upper surface and an enlarged head connected to the shaft, where the head is rotatable to extend over the aperture of the retaining member.

13. The system of claim 11, wherein the trailing portion of the rigid inner sleeve is configured to releasably lock within the aperture at a first position and wherein the trailing end of the flexible sleeve is configured to releasably lock within the aperture at a second position that is closer to the lower surface than the first position.

14. The system of claim 11, wherein the retaining member comprises a first projection and a second projection with both the first and second projections extending into the aperture, and the trailing portion of the rigid inner sleeve comprises a first recess and a second recess, wherein the first projection is sized to fit within the first recess and the second projection sized to fit within the second recess to releasably lock the trailing portion of the rigid inner sleeve within the aperture.

15. The system of claim 14, further comprising a locking switch on the retaining member that actuates to move the first and second projections into the aperture to fit within the respective first and second recesses.

16. A system for inserting and securing, through a suprapatellar region of a leg, an intramedullary nail into a medullary canal of a bone, the system comprising:
a flexible sleeve configured to be partially inserted in the leg, the flexible sleeve including a distal end, a proximal end, an elongated shaft and a proximal portion located proximally from the elongated shaft, the flexible sleeve defining a first cannulation extending between the proximal end and the distal end, the proximal portion having a first outer cross-section dimension greater than a maximum second outer cross-section dimension of the elongated shaft, the first cannulation sized to receive therethrough at least the intramedullary nail, wherein the flexible sleeve is configured to flex so as to change a shape of the elongated shaft from a first configuration to a second configuration, wherein the second configuration is different than the first configuration;
a rigid inner sleeve comprising an elongated shaft portion having a maximum, first, outer cross-sectional dimension and a trailing portion located proximally from the elongated shaft portion having a second cross-sectional dimension greater than the maximum, first, outer cross-sectional dimension;
a retaining device comprising a handle and a retaining member that extends from the handle, the retaining member having an upper surface and a lower surface and an aperture extending from the upper to the lower surface, the retaining member comprising first means for releasably locking the proximal portion of the flexible sleeve located adjacent to the aperture and between the upper and lower surfaces and second means for releasably locking the trailing portion of the rigid inner sleeve while the elongated shaft portion is disposed within the first cannulation of the flexible sleeve located adjacent to the aperture and between the upper and lower surfaces,
wherein the proximal portion of the flexible sleeve includes third means for releasably locking with the retaining member and the trailing portion of the rigid inner sleeve includes fourth means for releasably locking with the retaining member.

17. The system of claim 16, wherein the first means is located closer to the lower surface than the second means.

18. The system of claim 17, wherein the third means comprises a first detent and a second detent where the first and second detents are radially separated from one another.

19. The system of claim 18, wherein the first means comprises a first protrusion and a second protrusion where the first and second protrusions are formed along a perimeter of the aperture.

20. The system of claim 17, wherein the fourth means comprises a first recess and a second recess located in the trailing portion of the rigid inner sleeve.

21. The system of claim 20, wherein the second means comprises a first projection and a second projection, the first projection sized to fit within the first recess and the second projection sized to fit within the second recess.

22. The system of claim 21, further comprising a locking switch mechanically connected to the first and second projections where in a first position the locking switch urges the first and second projections into the aperture and in a second position the locking switch withdrawals the first and second projections out of the aperture.

23. The system of claim 17, further comprising a rotating blocking device located on the retaining member where the rotating blocking device comprises a shaft extending from the upper surface and an enlarged head connected to the shaft, where the head is rotatable to extend over the aperture of the retaining member.

24. A system for inserting and securing, through a suprapatellar region of a leg, an intramedullary nail into a medullary canal of a bone, the system comprising:
a flexible sleeve configured to be partially inserted in the leg, the flexible sleeve defining a leading end and a trailing end spaced apart from the leading end along a first axis, the flexible sleeve defining a first cannulation extending along the first axis between the leading and trailing ends, the first cannulation sized to receive therethrough at least the intramedullary nail, wherein the flexible sleeve is configured to flex so as to change a shape of the first axis from a first configuration to a second configuration, wherein the second configuration is different than the first configuration;
a rigid inner sleeve comprising a distal end, a trailing portion and an elongated shaft portion located between the distal end and the trailing portion;
a retaining device comprising a handle and a retaining member that extends from the handle, the retaining member configured to releasably lock to the trailing end of the flexible sleeve and further configured to releasably lock to the trailing portion of the rigid inner sleeve while the elongated shaft portion is disposed within the first cannulation of the flexible sleeve, wherein the retaining member is configured to position the flexible sleeve through the suprapatellar region of the leg such that the flexible sleeve leading end is aligned with a proximal end of the bone; and an intramedullary nail insertable through the flexible sleeve and into the medullary canal, wherein the intramedullary nail defines a proximal end and a distal end, and at least one curved portion that is disposed at least between the proximal and distal ends of the intramedullary nail, and the flexible sleeve is configured to flex as the nail is inserted from the trailing end to the leading end, wherein:

the retaining member comprises an upper surface and an opposed lower surface and an aperture extending from the upper surface to the lower surface where the aperture defines a center axis extending from the upper surface to the lower surface along a first direction;

the system further comprises an insertion device configured for removable connection to the intramedullary nail;

the intramedullary nail and at least a portion of the insertion device is configured to be received within the first cannulation of the flexible sleeve; and when 1) the insertion device is connected to the intramedullary nail, and 2) the flexible sleeve is inserted at least partially in the leg, the insertion device can advance the intramedullary nail through the flexible sleeve along the first direction to position the intramedullary nail in the medullary canal.

25. The system of claim 24, further comprising an aiming device connectable to the insertion device, the aiming device configured to guide at least one anchor toward the bone, wherein when 1) the aiming device is connected to the insertion device, and 2) the intramedullary nail is positioned in the medullary canal, the aiming device guides the at least one anchor toward the bone along a second direction that is transverse to the first direction.

26. The system of claim 25, wherein the insertion device further comprises an insertion member defining a leading end and a trailing end spaced apart from a leading end along a second axis, the insertion member defines an insertion member bore extending between the leading and trailing ends along the second axis, wherein the insertion member is configured to be at least partially disposed in the first cannulation of the flexible sleeve.

27. The system of claim 26, wherein the intramedullary nail defines a nail bore extending at least partially between the proximal and distal ends along a intramedullary nail direction, and one or more openings each configured to receive a portion of the at least one anchor, and the system further comprises a connecting rod configured to couple the insertion device to the intramedullary nail, wherein the connecting rod is configured to be at least partially disposed in the bore of the insertion member, wherein when the connecting rod is disposed at least partially in the bore of the insertion member, a portion of the connecting rod engages at least a portion of the intramedullary nail bore to connect the intramedullary nail to the insertion device.

28. The system of claim 26, wherein the proximal end of the intramedullary nail defines a notch, and the leading end of the insertion member defines a tab, wherein the tab is configured to be received by the notch so as to rotatably fix in the insertion member relative the intramedullary nail.

29. The system of claim 25, wherein the aiming device comprises an aiming member, and wherein the system further comprises a guide sleeve configured to be supported by the aiming member, wherein the guide sleeve defines a proximal end, a distal end spaced apart from an proximal end along a guide sleeve axis, and a guide sleeve cannulation extending between the proximal and distal ends along the guide sleeve axis, wherein the at least one anchor is insertable through the guide sleeve cannulation.

30. The system of claim 29, wherein the aiming member defines a first surface, a second surface spaced apart from the first surface along the second direction, and a plurality of channels extending between the first and second surfaces along the second direction, each channel configured to at least partially receive the guide sleeve therein.

31. The system of claim 30, wherein the aiming member is a frame that supports at least one extension member, the at least one extension member includes at least one of the plurality of channels, wherein when the aiming member is attached to the insertion device 1) the frame partially surrounds a portion of the leg, and 2) the at least one extension member extends along the first direction.

32. A system for inserting and securing, through a suprapatellar region of a leg, an intramedullary nail into a medullary canal of a bone, the system comprising:

a flexible sleeve configured to be partially inserted in the leg, the flexible sleeve defining a leading end and a trailing end spaced apart from the leading end along a first axis, the flexible sleeve defining a first cannulation extending along the first axis between the leading and trailing ends, the first cannulation sized to receive therethrough at least the intramedullary nail, wherein the flexible sleeve is configured to flex so as to change a shape of the first axis from a first configuration to a second configuration, wherein the second configuration is different than the first configuration;

a rigid inner sleeve comprising a distal end, a trailing portion and an elongated shaft portion located between the distal end and the trailing portion;

a retaining device comprising a handle and a retaining member that extends from the handle, the retaining member configured to releasably lock to the trailing end of the flexible sleeve and further configured to releasably lock to the trailing portion of the rigid inner sleeve while the elongated shaft portion is disposed within the first cannulation of the flexible sleeve, wherein the retaining member is configured to position the flexible sleeve through the suprapatellar region of the leg such that the flexible sleeve leading end is aligned with a proximal end of the bone, wherein:

the intramedullary nail is insertable through the flexible sleeve and into the medullary canal;

the retaining member comprises an upper surface and an opposed lower surface and an aperture extending from the upper surface to the lower surface, and the trailing end of the flexible sleeve is configured to releasably lock to the retaining member within the aperture of the retaining member and the trailing portion of the rigid inner sleeve is configured to releasably lock to the retaining member within the aperture of the retaining member; and the system further comprises a rotating blocking device located on the retaining member where the rotating blocking device comprises a shaft extending from the upper surface and an enlarged head connected to the shaft, where the head is rotatable to extend over the aperture of the retaining member.

33. A system for inserting and securing, through a suprapatellar region of a leg, an intramedullary nail into a medullary canal of a bone, the system comprising:

a flexible sleeve configured to be partially inserted in the leg, the flexible sleeve defining a leading end and a trailing end spaced apart from the leading end along a first axis, the flexible sleeve defining a first cannulation extending along the first axis between the leading and trailing ends, the first cannulation sized to receive therethrough at least the intramedullary nail, wherein the flexible sleeve is configured to flex so as to change a shape of the first axis from a first configuration to a second configuration, wherein the second configuration is different than the first configuration;

a rigid inner sleeve comprising a distal end, a trailing portion and an elongated shaft portion located between the distal end and the trailing portion;

a retaining device comprising a handle and a retaining member that extends from the handle, the retaining member configured to releasably lock to the trailing end of the flexible sleeve and further configured to releasably lock to the trailing portion of the rigid inner sleeve while the elongated shaft portion is disposed within the first cannulation of the flexible sleeve, wherein the retaining member is configured to position the flexible sleeve through the suprapatellar region of the leg such that the flexible sleeve leading end is aligned with a proximal end of the bone, wherein:

the intramedullary nail is insertable through the flexible sleeve and into the medullary canal;

the retaining member comprises an upper surface and an opposed lower surface and an aperture extending from the upper surface to the lower surface and the trailing end of the flexible sleeve is configured to releasably lock to the retaining member within the aperture of the retaining member and the trailing portion of the rigid inner sleeve is configured to releasably lock to the retaining member within the aperture of the retaining member; and the trailing portion of the rigid inner sleeve is configured to releasably lock within the aperture at a first position and the trailing end of the flexible sleeve is configured to releasably lock within the aperture at a second position that is closer to the lower surface than the first position.

34. A system for inserting and securing, through a suprapatellar region of a leg, an intramedullary nail into a medullary canal of a bone, the system comprising:

a flexible sleeve configured to be partially inserted in the leg, the flexible sleeve defining a leading end and a trailing end spaced apart from the leading end along a first axis, the flexible sleeve defining a first cannulation extending along the first axis between the leading and trailing ends, the first cannulation sized to receive therethrough at least the intramedullary nail, wherein the flexible sleeve is configured to flex so as to change a shape of the first axis from a first configuration to a second configuration, wherein the second configuration is different than the first configuration;

a rigid inner sleeve comprising a distal end, a trailing portion and an elongated shaft portion located between the distal end and the trailing portion;

a retaining device comprising a handle and a retaining member that extends from the handle, the retaining member configured to releasably lock to the trailing end of the flexible sleeve and further configured to releasably lock to the trailing portion of the rigid inner sleeve while the elongated shaft portion is disposed within the first cannulation of the flexible sleeve, wherein the retaining member is configured to position the flexible sleeve through the suprapatellar region of the leg such that the flexible sleeve leading end is aligned with a proximal end of the bone, wherein:

the intramedullary nail is insertable through the flexible sleeve and into the medullary canal;

the retaining member comprises an upper surface and an opposed lower surface and an aperture extending from the upper surface to the lower surface and the trailing end of the flexible sleeve is configured to releasably lock to the retaining member within the aperture of the retaining member and the trailing portion of the rigid inner sleeve is configured to releasably lock to the retaining member within the aperture of the retaining member; and the retaining member comprises a first projection and a second projection with both the first and second projections extending into the aperture, and the trailing portion of the rigid inner sleeve comprises a first recess and a second recess, wherein the first projection is sized to fit within the first recess and the second projection sized to fit within the second recess to releasably lock the trailing portion of the rigid inner sleeve within the aperture.

35. The system of claim 34, further comprising a locking switch on the retaining member that actuates to move the first and second projections into the aperture to fit within the respective first and second recesses.

* * * * *